US007713914B2

(12) United States Patent
Farquharson et al.

(10) Patent No.: US 7,713,914 B2
(45) Date of Patent: May 11, 2010

(54) METHOD FOR EFFECTING THE RAPID RELEASE OF A SIGNATURE CHEMICAL FROM BACTERIAL ENDOSPORES, AND FOR DETECTION THEREOF

(75) Inventors: Stuart Farquharson, Meriden, CT (US); Frank E. Inscore, Bristol, CT (US); Alan D. Gift, Lafayette, IN (US); Chetan Shrikant Shende, Vernon, CT (US)

(73) Assignee: Real-Time Analyzers, Inc., Middletown, CT (US)

(*) Notice: Subject to any disclaimer, the term of this patent is extended or adjusted under 35 U.S.C. 154(b) by 362 days.

(21) Appl. No.: 11/355,782

(22) Filed: Feb. 16, 2006

(65) Prior Publication Data

US 2006/0257891 A1 Nov. 16, 2006

Related U.S. Application Data

(60) Provisional application No. 60/654,664, filed on Feb. 18, 2005.

(51) Int. Cl.
*C40B 30/00* (2006.01)

(52) U.S. Cl. ................................................ 506/7; 435/5

(58) Field of Classification Search ....................... None
See application file for complete search history.

(56) References Cited

U.S. PATENT DOCUMENTS

| | | | |
|---|---|---|---|
| 5,876,960 | A | 3/1999 | Rosen |
| 6,838,292 | B1 | 1/2005 | Rajan et al. |
| 2005/0221418 | A1 | 10/2005 | Fell, Jr. et al. |

OTHER PUBLICATIONS

"Detecting *Bacillus cereus* Species on a Mail Sorting System Using Raman Spectroscopy" Stuart Faquharson, et al. (Journal of Raman Spectroscopy, 2004; 35:82-86).

"Chemical Agent Detection by Surface-Enhanced Raman Spectroscopy," Stuart Farquharson et al., Real-Time Analysers, Inc.

"Rapid Dipicolinic Acid Extraction from *Bacillus* Spores Detection by Surface-Enhanced Raman Spectroscopy" Stuart Farquharson et al. (Applied Spectroscopy, 2004; 58:351-354).

"Chelation Number of Terbium Dipicolinate: Effects on Photoluminescence Lifetime and Intensity" David L. Rasen et al, (Applied Spectroscopy, 2001;55:208-216).

"Bacterial Endospore Detection Using Terbium Dipicolinate Photoluminescence in the Presence of Chemical and Biological Materials" Paul M. Pellegrino et al.(Analytica Chimica Acta 455 (2002) 167-177).

"Enhanced Spore Detection Using Dipicolinate Extraction Techniques" Paul M. Pellegrino et al. (Analytica Chimica Acta 455 (2002) 167-177).

"Differentiating Bacterial Spores From Hoax Materials by Raman Spectroscopy" Stuart Farquharson et al., Real-Time Analyzers, Inc.

"Bacterial Spores and Chemical Spermicidial Agents" A. D. Russell (Clinical Microbiology Reviews, Apr. 1990, p. 99-119) vol. 3, No. 2.

"Germination of Spores of *Bacillus subtilis* With Dodecylamine" B. Setlow, et al. (Journal of Applied Microbiology 2003, 95, 637-648).

"Mechanisms of Killing Spores of *Bacillus subtilis* by Acid, Alkali and Ethanol" B. Setlow, et al. (Journal of Applied Microbiology. 2002, 92, 362-375).

"Mechanisms of Killing Spores of *Bacillus subtilis* by Iodine, Glutaraldehyde and Nitrous Acid" R. Tenne, et al. (Journal of Applied Microbiology 2000, 89, 330-338).

"Mechanisms of Killing of *Bacillus subtilis* Spores by Hypochlorite and Chlorine Dioxide" S.B. Young et al. (Journal of Applied Microbiology 2003, 95, 54-67).

"Rapid Detection of an Anthrax Biomarker by Surface-Enhanced Raman Spectroscopy" Xiaoyu Zhang, et al. (J. Am. Chem. Soc.-2005, 127, 4484-4489).

*Primary Examiner*—Jeffrey S. Lundgren
(74) *Attorney, Agent, or Firm*—Ira S. Dorman

(57) ABSTRACT

A weak organic acid is used to effect the release of CaDPA from *Bacillus* or *Clostridium* endospores, rapidly and at room temperature, to enable detection and measurement of DPA and thereby the assessment of risk associated with exposure to *Bacillus anthracis, Clostridium botulinum*, and like spores. The method can be applied to airborne, food-borne, and water-borne spores, as well as to spores collected from surfaces or contained in body fluids, and analysis is advantageously carried out using surface-enhanced Raman spectroscopy.

41 Claims, 6 Drawing Sheets

DPA from 1 μg B. cereus particle using:
A) Acetic Acid
B) Formic Acid
C) Lactic Acid
D) Trifluoroacetic acid DPA from 10 μg B. cereus particle using DDA:
A) Hot (78 °C)
B) RT (25 °C)
Minutes
60
40
20
10
5

METHOD FOR EFFECTING THE RAPID RELEASE OF A SIGNATURE CHEMICAL FROM BACTERIAL ENDOSPORES, AND FOR DETECTION THEREOF

CROSS REFERENCE TO RELATED APPLICATION

This application claims the benefit of U.S. Provisional Patent Application No. 60/654,664, filed Feb. 18, 2005 in the names of the same inventors.

STATEMENT REGARDING FEDERALLY SPONSORED RESEARCH AND DEVELOPMENT

The U.S. Government has rights in this invention pursuant to US Army Contract No. DAAD13-02-C-0015, NSF Contract No. DMI-0214280 and NSF Contract No. DMI-0215819.

BACKGROUND OF THE INVENTION

Calcium dipicolinate (CaDPA, calcium 2,6-pyridinedicarboxilate) represents 5 to 15% by weight of *Bacillus anthracis* spores (Murrell, W G, in *The Bacterial Spores*, Gould, G W, A Hurst, Eds. Academic Press, London, 1969, p. 215), and consequently a number of methods are being developed and used to detect CaDPA or its derivatives as an indicator or biochemical signature for the presence of *B. anthracis*, a bacterium that has been used in bioterrorism due to its ability to cause anthrax. The appropriateness of measuring CaDPA or its derivatives as a signature for *B. anthracis* is supported by the fact that only spore-forming bacteria contain CaDPA, of which there are 13 genera, two of which, *Bacillus* and *Clostridium*, are common and of interest; while the most widespread, potentially interfering spores, such as pollen and mold spores, do not contain CaDPA. This ability to discriminately detect anthrax-causing spores is one of the important measurement parameters that must be satisfied if a method is to have value in minimizing terror. Three additional germane measurement parameters include sensitivity, speed and ease-of-use. The Center for Disease Control estimates that inhalation of 10,000 spores, or 100 nanograms, will be lethal to 50 percent of an exposed population (Ingelsby, T V et al., "Anthrax as a biological weapon, 2002: Updated recommendations for management" *J Amer Med Ass,* 287, 2236-52, 2002). The ideal measurement device would have as a minimum sensitivity the ability to detect the presence of 10,000 spores within minutes of detection, such that precautions could be executed to prevent infection. Such a device could be used to detect spores in suspicious mail or on contaminated surfaces, and prevent distribution or exposure.

Methods that have successfully been used to detect CaDPA or its derivatives include mass spectrometry and fluorescence, luminescence, and Raman spectroscopies. Mass spectrometry has been used to identify dipicolinic acid (DPA), the acid form of CaDPA, that was separated from spores by pyrolysis (Beverly M B, F Basile, K J Voorhees, T L Hadfield, "A rapid approach for the detection of dipicolinic acid in bacterial spores using pyrolysis/mass spectrometry", *Rapid Commun. Mass Spectrom,* 10, 455-458, 1996). Although this method provides a relatively high degree of discrimination and sensitivity, it requires significant time due to sample handling and data analysis.

Fluorescence involves of course the absorption of electromagnetic radiation into an electronic transition of a molecule and the re-emission of radiation at longer wavelengths. It has been shown that fluorescence can be obtained from CaDPA (Nudelman, R, B V Bronk, S Efrima, "Fluorescence Emission Derived from Dipicolinate Acid, its Sodium, and its Calcium Salts" *Appl Spectrosc* 54, 445-449, 2000), however the emission spectrum is not sufficiently unique to differentiate it from common biological materials that also fluoresce. In an effort to overcome this limitation, others have explored the formation and the use of a terbium-DPA complex to generate a distinctive, highly luminescence spectrum (here defined as fluorescence that employs a chemical modification, Rosen D L, C Sharpless, L B McBrown, "Bacterial spore detection and determination by use of terbium dipicolinate photoluminescence", *Anal Chem,* 69, 1082-1085, 1997; or Rosen D L et al. U.S. Pat. No. 5,876,960). In a similar study, hot dodecylamine (DDA, a cationic surfactant) was used to rapidly break apart the spore to release CaDPA, as the acid, to form the terbium complex (Pellegrino P M, N F Fell Jr., J B Gillespie, "Enhanced spore detection using dipicolinate extraction techniques" *Analyt Chim Acta,* 455, 167-177, 2002). Unfortunately, it has been found that as many as three concentration-dependent complexes can form, each with different lifetimes (Rosen D L, S Niles, "Chelation Number of Terbium Dipicolinate: Effects on Photoluminescence Lifetime and Intensity", *Appl Spectrosc* 55, 208-216, 2001). This, coupled with the fact that the $Tb^{3+}$ cation produces the same luminescence spectrum, makes determinations of low spore concentrations problematic. Furthermore, the combination of heat and the DDA surfactant severely degrade the spore, generating cell debris (here defined as biochemical fragments of the spore). This requires sample cleanup and in this particular case, $AlCl_3$ had to be added to remove phosphates that would interfere with the photoluminescent measurement.

It has long been known that Raman spectra of bacilli spores are dominated by peaks associated with CaDPA, and that these spectra may provide a suitable anthrax signature at the genus level (Woodruff W H, T G Spiro, C Gilvarg, "Raman Spectroscopy In Vivo: Evidence on the Structure of Dipicolinate in Intact Spores of *Bacillus Megaterium", Biochem Biophys Res Commun,* 58, 197-203, 1974). Since that time, considerable improvements in Raman instrumentation have led to field measurements of spores captured from a mail-sorting system (Farquharson S, L Grigely, V Khitrov, W W Smith, J F Sperry, G Fenerty, "Detecting *Bacillus cereus* spores on a mail sorting system using Raman Spectroscopy", *J Raman Spectrosc,* 35, 82-86, 2004). However, Raman spectroscopy is inherently an insensitive technique, and these measurements were of milligram, and not the required nanogram, sample amount.

Two approaches are widely used to improve the sensitivity of Raman spectroscopy, i.e., resonance Raman spectroscopy and surface-enhanced Raman spectroscopy (SERS). The former method involves laser excitation at or near the wavelength of an electronic absorption to substantially increase the interactions between the radiation and molecular states, and was used more than a decade ago to analyze *Bacillus* spores (Ghiamati E, R S Manoharan, W H Nelson, J F Sperry, "UV Resonance Raman spectra of *Bacillus* spores", *Appl Spectrosc,* 46, 357-364, 1992). The value of this technique is limited by the extremely low energy conversion of ultraviolet lasers, which require substantial power supplies and thus confine measurements to laboratory settings, and which also require spectral acquisition times as long as one hour.

SERS involves the absorption of incident laser photons within nanoscale metal structures, generating surface plasmons, which couple with nearby molecules (the analyte) and thereby enhance the efficiency of Raman scattering by six orders of magnitude or more (Jeanmaire D L, R P Van Duyne, "Surface Raman Spectroelectrochemistry", *J Electroanal Chem,* 84, 1-20, 1977; or Weaver M J, S Farquharson, M A Tadayyoni, "Surface-enhancement factors for Raman scattering at silver electrodes: Role of adsorbate-surface interactions and electrode structure", *J Chem Phys,* 82, 4867-4874, 1985). In addition to affording high levels of sensitivity, the rich molecular vibrational information provided by Raman scattering yields exceptional selectivity and allows the identification of virtually any chemical as well as the ability to distinguish multiple chemicals in mixtures (see Garrel R L, "Surface-Enhanced Raman Spectroscopy", *Anal Chem,* 61, 401A-411A, 1989; or Storey J M E, T E Barber, R D Shelton, E A Wachter, K T Carron, Y Jiang, "Applications of Surface-Enhanced Raman Scattering (SERS) to Chemical Detection", *Spectroscopy,* 10, 20-25, 1995).

Four methods have become common in the practice of generating SERS. They are: (1) activated electrodes in electrolytic cells (see for example Jeanmaire or Weaver above); (2) activated silver and gold colloids (Kerker M, O Siiman, L A Bumm, D-S Wang, "Surface-enhanced Raman Scattering of citrate ion adsorbed on colloidal silver", *Appl Opt,* 19, 3253-3255, 1980, or Angel S M, L F Katz, D D Archibold, L T Lin, D E Honigs, "Near Infrared Surface-enhanced Raman Spectroscopy. Part II: Copper and gold colloids", *Appl Spectrosc,* 43, 367-372, 1989); (3) activated silver and gold substrates (Seki H, "Surface-enhanced Raman Scattering of pyridine on different silver surfaces", *J Chem Phys,* 76, 4412-4418, 1982, or Li Y-S, T Vo-Dinh, D L Stokes, Y Wang, "Surface-Enhanced Raman Analysis of p-Nitroaniline on Vacuum Evaporation and Chemical Deposited Silver-Coated Alumina Substrates", *Appl Spectrosc,* 46, 1354-1357, 1992); and (4) sol-gels doped with silver or gold particles (Farquharson et al. U.S. Pat. Nos. 6,623,977, 6,943,031, and 6,943,032 and corresponding International Application Publication No. WO 01/33189 A2, which are commonly owned herewith and the entire specification of which the United States patents are hereby incorporated by reference thereto).

The first measurement of dipicolinic acid by SERS was reported in 1999 followed by a more in-depth analysis in 2004 (Farquharson S, W W Smith, S Elliott, J F Sperry, "Rapid biological agent identification by surface-enhanced Raman spectroscopy", *SPIE,* 3855, 110-116, 1999; Farquharson S, A Gift, P Maksymiuk, F Inscore, and W Smith, "pH dependence of methyl phosphonic acid, dipicolinic acid, and cyanide by surface-enhanced Raman spectroscopy", *SPIE,* 5269, 117-125, 2004). In these two reports, the measurement of DPA by SERS was performed to demonstrate the possible use of such a measurement to identify spores, such as *Bacillus anthracis*. However, both measurements were of pure DPA in water and no method to extract the DPA from spores was mentioned. In any event, no prior art describes the use of chemicals to cause the release of CaDPA so that it or DPA is available for measurement by SERS; that concept is disclosed in recent papers authored by the present inventors (see Farquharson S, A Gift, P Maksymiuk, F E Inscore, "Rapid dipicolinic acid extraction from *Bacillus* spores detected by surface-enhanced Raman spectroscopy", *Appl Spectrosc,* 58, 351-54, 2004; and Inscore F E, A D Gift, S Farquharson, "Detect-to-treat: development of analysis of *Bacilli* spores in nasal mucus by surfaced-enhanced Raman spectroscopy", *SPIE,* 5585, 53-57, 2005).

Since the Farquharson, et al. publication (*Appl Spectrosc,* 2004) one research group has attempted to improve upon these measurements (Zhang X, M A Young, O Lyandres, R P Van Duyne, "Rapid Detection of an Anthrax Biomarker by Surface-Enhanced Raman Spectroscopy", *J Am Chem Soc,* 127, 4484-4489, 2005). In this paper, published on Mar. 30, 2005, 0.02M nitric acid was used in conjunction with 10 minutes of ultrasonification to obtain a SER spectrum of DPA. Although a 200 fold improvement in sensitivity was claimed, the lowest reported amount measured, 187,000 spores per microliter, was considerably less sensitive than the 10,000 spores per microliter reported by Farquharson et al. Xhang et al. also reported that no signal was obtained unless sonication was used.

Even so, in these measurements, the use of DDA or nitric acid alone was insufficient to separate a significant amount of DPA (defined, for present purposes, to be at least 10% by weight, on average, of that which is available) in a timely manner (defined, for present purposes, as a period that is less than 30 minutes, and preferably less than 10 minutes), without the addition of heat or ultrasound. The use of heat or ultrasound had two deleterious consequences, 1) it produced spore debris that likely reduced the sensitivity of the SERS measurement, and 2) it unduly complicated the device by requiring a heat or ultrasound source.

Significant research to understand the sporulation and corresponding germination of spores has been performed for more than 50 years. Bacterial spores are considered marvels of nature, in that when conditions for life become unfavorable, they become dormant through a process known as sporulation (forming an endospore). These spores are resistant to severe environmental conditions, such as heat, ultraviolet radiation, vacuum, and many chemicals including oxidizing agents and strong acids (e.g. nitric, hydrochloric, sulfuric, etc., see Russell, A D, *The destruction of bacterial spores*, Acad Press, New York, N.Y., 1982 or Nicholson, et al. "Resistance of *Bacillus* Endospores to Extreme Terrestrial and Extraterrestrial Environments", *MicroBio Molec Bio Rev,* 64, 584-572, 2000). However, when conditions are again favorable they re-initiate cell growth through a process known as germination (see Dricks, A, "From Rings to Layers: Surprising patterns of protein deposition during bacterial spore assembly", *J Bacteriol,* 186, 4423-4426, 2004). Numerous methods have been examined to initiate germination to elucidate this process. Germinants studied naturally included amino and nucleic acids, sugars, carbohydrates, and also dodecylamine (Setlow B, A E Cowan, P Setlow, "Germination of spores of *Bacillus subtilis* with dodecylamine", *J Appl Microbiol,* 95, 637-648, 2003). It is now known that certain amino acids and inosine, a nucleic acid variant, initiate germination, which includes an early step involving the release of CaDPA, which becomes DPA as it enters the surrounding solution. It is also now known that DDA initiates germination through a different mechanism. The details of these mechanisms whereby CaDPA is released using natural nutrients or DDA, through one or multiple spore wall channels, are still unknown. In fact, endospores may contain a small percent of DPA along with the CaDPA. In either case, however, germination takes several hours at room temperature, and consequently none of these chemicals provide sufficient speed for the purpose to satisfy the objects of this invention.

In another area of research, methods have been investigated for the purpose of killing spores, such as in the case of sterilizing medical equipment and disinfecting food. A comprehensive review is given by Russel A D, "Bacterial Spores and Chemical Sporicidal Agents", *Clin Microbiol Revs,* 3, 99-119, 1990. In summary, only few chemicals kill spores effectively, glutaraldehyde, formaldehyde, chlorine releasing agents, peroxygens (e.g. peroxide), and ethylene oxide, of which only the first two have practical value. It is worth noting that according to this review organic acids, specifically, benzoic acid and sorbic acid, can be used to kill bacterial cells, but not spores. In recent years the mechanisms by which these chemicals, and others, kill spores have been examined. However, only limited studies have involved the analysis of DPA. These reports measure the release of DPA as a method of improving the understanding of germination, as well as spore death. These reports include the use of inorganic acids, alkali, peroxides, and haloginated chemicals (Young S B, P Setlow, "Mechanisms of killing of spores of *Bacillus subtilis* by iodine, glutaraldehyde and nitrous acid", *J Appl Microbiol,* 89, 330-338, 2000, Setlow B, C A Loshen, P C Genest, A E Cowan, C Setlow, P Setlow, "Mechanisms of killing spores of *Bacillus subtilis* by acid, alkali, and ethanol", *J Appl Microbiol,* 92, 362-375, 2002, and Young S B, P Setlow, "Mechanisms of killing of *Bacillus subtilis* spores by hypochlorite and chlorine dioxide", *J Appl Microbiol,* 95, 54-67, 2003). In all of these cases, hours of treatment are required to generate significant quantities of DPA. Again, however, the inclusion of a physical means, such as heat, pressure, sonication, or their combination (e.g. autoclaving), are required if the DPA release times are to be substantially reduced, and in such cases significant cell debris is generated, thus compromising the sensitivity of DPA detection.

It is therefore surprising that treatment of spores by a weak acid compound, having a pKa value of 0.1 to 11, at room temperature, in accordance with the present invention and as is described hereinafter, quickly (e.g., within 10 minutes) releases most, if not all, of the CaDPA contained therein.

SUMMARY OF THE INVENTION

It is a broad object of the present invention to provide a novel method for rapidly obtaining information to aid in the assessment of health risks associated with exposure to spores, and in particular spores of the genera *Bacillus* or *Clostridium.*

It is also an object of the invention to provide a method for the detection, identification, and semi-quantitative determination of the analyte chemical, obtained as described herein, by any suitable analytical instrument means, such as mass or ion mobility spectrometry; electrophoresis; fluorescence, phosphorescence, photo-luminescence, infrared, Raman or surface-enhanced Raman spectroscopy; combinations of such means; and other means commonly known to those skilled in the art of detecting trace chemicals (e.g. chromatography).

It is a more specific object to provide such a method wherein a biological signature chemical, such as in particular calcium dipicolinate (CaDPA), is released from endospores in an analytically detectable form, such as itself or, in particular, in the form of dipicolinic acid (DPA), protonated or deprotonated.

A further specific objective of the invention is to provide a novel method in which one or more weak acid compounds, having a pKa value of 0.1 to 11, is employed to release the signature chemical from the endospores, and in which additional physical means, such as heat or sonication, are not required to ensure release of the signature chemical in a timely manner, e.g., within 10 minutes.

It has now been found that certain of the foregoing and related objects of the invention are attained by the provision of a novel method, which comprises the steps: obtaining a sample comprised of at least one species of bacteria having endospores containing a signature chemical; combining, with at least a component of the sample containing the bacteria, an effective amount of an acidic composition providing, in solution, at least one weak acid compound having a dissociation constant of 0.1 to 11, expressed as its pKa value, so as to produce a liquid mixture; and allowing the weak acid compound to interact with the endospores for a period of time and under conditions sufficient to effect release from the endospores of an analytically detectable form of the signature chemical as an analyte chemical, to thereby produce an analyte substance containing the analyte chemical.

The species of bacteria to which the method of the invention is applied will usually be of the genera *Bacillus* or *Clostridium*, and in particular the species *Bacillus anthracis*. The signature chemical involved will, in such instances, normally be calcium dipicolinate and the analyte chemical involved will be dipicolinic acid. The weak acid compound utilized will usually be a $C_1$ through $C_{16}$ acid, generally a carboxylic acid and, more particularly, an acid selected from the group consisting of acetic, adipic, ascorbic, citric, formic, fumaric, lactic, malic, palmitic, peracetic, propionic, salicylic, sorbic, succinic, and trihaloacetic acids (e.g., trifluoroacetic acid), and mixtures thereof; preferably, the weak acid utilized will be acetic acid. The weak acid compound may however also be supplied as a normally solid composition, e.g., sodium acetate or ethylene diamine tetraacetic acid, and the acidic composition may be an aqueous or organic solvent solution containing from about 0.1 to 95 weight percent of the weak acid-forming ingredient; suitable organic solvents include acetone, acetonitrile, benzene, chloroform, carbon tetrachloride, cyclohexane, dichloromethane, diethyl ether, dimethylsulfoxide, ethanol, ethyl acetate, ethylene glycol, isopropyl ether, methanol, methyl ethyl ketone, n-hexane, tetrahydrofuran, toluene, and mixtures thereof.

In preferred embodiments, the step of releasing the analyte chemical will be effected at ambient temperature, normally 20° to 25° Centigrade, albeit a temperature mildly elevated above ambient, i.e., a temperature not higher than 50° Centigrade, may desirably be employed. The time of interaction of the weak acid with the endospores will not usually exceed 30 minutes, and preferably the period will be from 1 to 10 minutes, albeit in some instances a period of only 10 seconds may suffice. The liquid mixture in which spore interaction occurs will generally contain at least 10 percent by weight thereof of the weak acid compound, and it will be appreciated that the liquid component may be supplied by the acidic composition, by the bacteria-containing sample, or both.

The sample utilized in carrying out the method may be obtained from ambient air (e.g., as a collected aerosol), water, food, a physical surface of an object or structure, or the body of an animal. In most cases the sample will comprise a human body fluid (i.e., nasal mucus, throat sputum, saliva or sweat), in which instances the method will desirably include the further step of separating the bacteria from other components of the body fluid, to provide the "at least a component" of the sample containing the bacteria. Such a separation step is advantageously performed by admixing with the body fluid a degrading chemical selected from the group consisting of mucolytic agents, surfactants, solvents, acids and bases, and mixtures thereof; suitable mucolytic agents include N-acetyl-L-cysteine, Amboxol, Bromhexine, and combinations thereof, and a solution of N-acetyl-L-cysteine and NaOH, is presently preferred.

Additional objects of the invention are attained by the provision of a method that includes a further step of subjecting the analyte substance to analysis for determining at least the presence (but preferably also the quantity) of the analyte chemical in the analyte substance. Such an analysis will generally be performed by mass or ion mobility spectrometry; by electrophoresis; by fluorescence, phosphorescence, photoluminescence, infrared, Raman, or surface-enhanced Raman spectroscopy (SERS); or by gas, liquid or high-performance liquid chromatography; or combinations thereof. Preferably, however, analysis will be performed by surface-enhanced Raman spectroscopy, with the method including the further step of combining the analyte substance with a SERS-active medium, the SERS-active medium thereafter being subjected to irradiation and being used as the source from which surface-enhanced Raman radiation is collected, in performing the analysis.

A SERS-active medium will, in general, consist of a SERS-active metal in the form of particulates or other appropriately sized structures that can support a surface plasmon field. The SERS-active metal will normally be selected from the group consisting of copper, gold, silver, and alloys and mixtures thereof, and the SERS-active medium will generally be of a form selected from metal colloids in solution, metal colloids deposited on surfaces, metal-coated particles on a surface, metal depositions on surface structures, electrochemically generated metal surfaces, and metal-doped porous materials, in particular metal-doped sol-gels. Preferably, such a metal-doped sol-gel will be sufficiently porous to permit the analyte substance to be transported therethrough so as to effectively separate the analyte chemical from other components of the analyte substance, with at least a portion of the analyte chemical being retained in the sol-gel in sufficiently intimate proximity to the dopant metal to enable generation, in the irradiation step, of surface-enhanced Raman spectra of the analyte chemical.

Porous materials that contain SERS-active metals can be produced by chemical synthesis, using methods that include sol-gel chemical syntheses employing silica-based alkoxides and SERS-active metals, and polymer syntheses employing hydrophilic monomers that allow the inclusion of SERS-active metals. The SERS-active medium may also be a porous volume produced by mixing a porous medium and a SERS-active metal; such media include sol-gels, silica gels, silica stabilized by zirconia, derivatized silica-based matrices (e.g., trifunctional quaternary amine, aromatic sulfonic acid), long-chain alkane particles (e.g., $C_8$ to $C_{18}$), derivatized long-chain alkane particles (e.g., phenyl, cyano, etc.), and other porous media commonly known to one skilled in the art of porous media.

Such a sol-gel will advantageously be of a chemical composition that is effective to extract the analyte chemical from the analyte substance, to thereby improve sensitivity. For the same reason, the dopant metal of the sol-gel may desirably have an electro-potential that is effective to attract the analyte chemical from the analyte substance, e.g., electropositive silver effective to attract a negatively-charged, deprotonated acidic analyte chemical.

As noted, in especially preferred embodiments of the invention the analysis method will be effective to determine the quantity of the analyte chemical in the analyte substance. In such embodiments, a known amount of the weak acid compound will be employed in the step of interacting with the endospores, so as to enable quantification. Quantitative analysis is limited however by the amount of the signature chemical present in the spores under investigation, which will generally range (using CaDPA as typical) from 5% to 15% by weight, and on average 10% by weight. Such a method will advantageously include the additional step of passing the analyte substance though a material that is effective to remove residual spore components and cell debris, such as a filter, a membrane, a chromatography material and a sol-gel.

The ability of weak acids to release CaDPA (or other signature chemicals) from endospores, without requiring physical aids such as high temperatures, ultrasound, or the like, overcomes limitations of prior techniques that do require such methods and apparatus, while also serving to avoid the production or accumulation of associated cell debris that is generated thereby, such debris having been found to interfere with analysis or to limit measurement sensitivity. As used herein, a weak acid is defined as an acid having a dissociation constant, Ka, of between $10^{-0.8}$ and $10^{-11}$, or, stated otherwise, to have a pKa between 0.1 and 11. Suitable weak acids include all mono-, di-, tri- and tetra-carboxylic acids ($C_1$ through $C_{16}$), branched or straight-chained, aliphatic, aromatic, or substituted acids, as well as their salts (e.g., sodium acetate) that produce such acids when added to water or another solvent or solvent mixture. In the preferred embodiments, acetic, citric, formic, fumaric, lactic, malic, propionic, sorbic, tetraacetic, trifluoroacetic acid, or a mixture thereof, with or without solvents, would be used.

In general, the present invention employs a sequence of steps for rapidly identifying the presence of the signature chemical at concentrations meaningful in the assessment of risk associated with exposure to endospores; the steps include: 1) acquiring a sample for measurement; 2) treating the sample with a weak acid compound to cause the release of the signature chemical, or an analytically detectable form thereof, 3) presenting the analyte chemical to an analytical instrument (or other means for analysis); 4) identifying and quantifying the analyte chemical with the analytical instrument or other means; and 5) presenting the analysis as appropriate (e.g. displayed, recorded, or transmitted data, warnings, etc.). It will be appreciated that CaDPA and DPA (protonated, mono-protonated or deprotonated) are representative, respectively, of the signature chemicals and analyte chemicals to which the specification and claims refer, and are indeed the chemicals that are presently regarded to be singularly important in carrying out the method; as noted, however, CaDPA may itself be analytically detectable, and thus may constitute both an analyte chemical and also a signature chemical. The same principles and considerations are believed to apply, moreover, to other chemicals that are contained in, and can be caused to be released from, bacteria; e.g., n-acetyl-glucosamine, deoxyribonucleic, diaminopimelic, n-acetylmuramic, ribonucleic, phosphoglyceric, and sulfoactic acids, derived from *Bacillus anthracis* or *Clostridium botulinum*.

In one use of the present invention, a surface suspected of being contaminated with endospores, such as those associated with mail facilities (bins used to hold letters, sorting equipment, etc.), is examined to detect *Bacillus anthracis* spores. A drop of the weak acid compound employed is applied to the surface and allowed to interact with any bacteria present, typically for one minute, to cause the release of CaDPA into the solution and to form DPA. The DPA produced is drawn by syringe through a filter, so as to exclude leftover spore casings or spore debris, into a sample container, which is then placed within, or attached to, the sample compartment of any suitable analytical instrument (as described herein), and the required measurement is performed.

A drop of liquid is defined, at least for present purposes, to be a volume of 50 microliters. Since the amount of acid used in the present procedures would generally be known, that information can be used, in conjunction with knowledge of the measured surface area covered, to quantify the spores detected (e.g. 10 spores per $cm^2$). As an alternative, a swab could be used to wipe a predefined area, which is then introduced into a predefined volume of weak acid so as to again quantify the measurement.

A variety of devices can be employed to dispense the weak acid, to collect the resultant analyte solution, and to deliver the solution to a sample container. For example, a simple eyedropper, a disposable pipette, a calibrated micropipetter, or a calibrated syringe could be used both to dispense the acid and also to collect the solution (analyte substance), or another syringe, desirably fitted with a particle and/or chemical filter, could be used for collection. In the specific case in which acetic acid is used to release CaDPA, a calibrated syringe, used to deposit 50 microliters, is presently preferred. And, while the acetic acid interacts with (or acts upon) any spores that might be present, the syringe, now fit with a filter holder that contains a polytetrafluoroethylene (PTFE) ultrafilter designed to capture protein-sized particles, for removing them from the DPA containing solution, will be preferred in some instances.

In a second manner of use of the present method, air samples are continuously or periodically collected and examined for spores, and any apparatus that is commonly used to collect and concentrate particles from the air can serve as a sample-acquisition device. In many instances, however, cyclone or impactor devices will be preferred, which may be designed to handle large volumes of air at high flow rates and to collect particles within certain size ranges, such as biological particles of 1-20 microns. In any event, such an airborne sample acquisition device would advantageously deposit the collected particles into a vessel containing a weak acid, to allow interaction for a predefined period of time so as to effect the release of CaDPA for analysis, as previously described.

In the case of continuous monitoring, the collected spores could also be deposited upon a rotating carousel holding numerous containers of weak acid, or into a flowing stream of the weak acid, or upon a moving tape to which the weak acid is added. In the case of the carousel, each container could be analyzed as described above, manually or automatically. In the case of a flowing acid stream, the sample could be passed through a filter to remove spores or other collected particles, and then be passed into a sample flow-cell placed within or attached to the sample compartment of any of the analytical instruments described above, to enable the required measurement to be performed. In the case of a moving tape, an appropriately placed source of weak acid could be added to release the CaDPA, such that the DPA is available for collection from the tape and passage into a sample flow-cell for analysis. It will also be appreciated by those skilled in the art that wet-walled cyclones, designed to efficiently capture particles and transfer them to a container below, could be used to particularly good advantage; the weak acid used for analyte release could then serve as the wall-washing solution.

In another mode of use of the instant method, the spore-containing sample is obtained from nasal mucus, throat sputum, saliva or sweat; samples may of course be acquired using a swab, by rinsing, by scraping, or by collection of substances produced by spiting or nose blowing. In such cases, additional means may be desirably employed to separate the spores from the body fluid prior to addition of the weak acid. When a swab is used to collect a sample, the swab would be weighed before and after swabbing, to determine the sample mass and to allow quantifying results; non-cotton swabs (e.g., of polyester) will generally be preferred, since cotton fibers tend to plug pores of separation media. Similarly, implements used for collection by other means will of course be weighed before and after collection to determine the sample mass and to allow quantifying results.

Nasal mucus and sputum are composed largely of water (about –95%) and mucins, otherwise known as glycoproteins (about 0.5-2%) (Kaliner, M, Z Marom, C Patow, "Human respiratory mucus", *J Allergy Clin Immunol,* 73, 318-323, 1984). The mucins consist of a protein core (about 20%) with oligosaccharide side chains (about 80%), crosslinked by disulfide and hydrogen bonds, which give mucus, sputum and saliva its high viscosity.

The mucins must be broken down, or "liquefied," to separate any spores that may be present (see for example; Kubica, G, A Kaufmann, W Dye, "Comments on the use of the new mucolytic agent, N-acetyl-L-cysteine, as a sputum digestant for the isolation of mycobacteria", *Am Rev Respir Dis,* 87, 775-779, 1964; or Murray, P, E Baron, J Jorgensen, M Pfaller, R Yolken, *Manual of Clinical Microbiology,* $5^{th}$ ed, ASM Press, Washington D.C., 1995).

Nasal mucus may be chemically degraded, to allow mutual separation of the spores and nasal mucus degradants, using mucolytic agents, surfactants, acids and/or bases. Suitable mucolytic agents include N-acetyl-L-cysteine (NALC), Amboxol, Bromhexine, or any combination thereof; preferably, a solution of N-acetyl-L-cysteine and NaOH will be employed. The surfactant utilized may advantageously be lithium dodecyl sulfate, sodium dodecyl sulfate or, a combination thereof, and the acid or base employed may be HCl, $H_2SO_4$, $HNO_3$, NaOH, or KOH, or any combination consisting of such acids or bases.

Nasal mucus degradants and spores may be separated by chemical, physical, or chromatographic treatments, or any combination thereof. Chemical treatments will typically employ a solvent, such as water having a selected pH value, acetone, acetonitrile, benzene, chloroform, carbon tetrachloride, cyclohexane, dichloromethane, diethyl ether, dimethylsulfoxide, ethanol, ethyl acetate, ethylene glycol, isopropyl ether, methanol, methyl ethyl ketone, n-hexane, tetrahydrofuran, toluene, and mixtures thereof, especially those mixtures that aid in selectively extracting the spores into a desired solvent.

Physical treatments that may be employed for separation of spores include filtration, chromatography, and centrifugation, with suitable filters being comprised of a porous substrate such as, for example, paper, coated paper, paper fibers, polymer, polymer fibers, mixed paper and polymer fibers, cellulose acetate, glass wool, cotton, diatomite, porous glass, sintered glass, zirconia-stabilized silica, derivatized silica-based matrices, sol-gels, and derivatized sol-gels. The filters may also be comprised of a supported membrane covered with a separation material such as a silica gel, zirconia-stabilized silica, derivatized silica-based matrices, sol-gels, derivatized sol-gels, agarose, glass beads, long-chain alkane particles, derivatized long-chain alkane particles, polymers, derivatized polymers, functionalized membranes, alumina, polystyrene, dendrimers, immobilized crown ethers, and ion-exchange resins. Chromatographic methods may employ the same separation materials.

Heretofore, a chemical method used to break open endospores and release CaDPA into solution employed a surfactant such as dodecylamine (DDA), dodecylamine chloride, sodium dodecyl sulfate, N-dodecyl-N,N-dimethyl betaine, and TritonX-100, preferably heated; e.g., 5 mM DDA heated to 78° C. was found to be effective. Physical methods that were used to break open endospores, and release CaDPA into solution, include ultrasound, heat, and high-pressure devices (e.g., a French press). Due to the time and temperature conditions required, however, and the need for augmentation of the CaDPA-releasing mechanism procedures, based upon the use of DDA and functionally equivalent chemicals, are not regarded to be entirely satisfactory.

In the embodiments of the present invention described, the sample container will preferably include a SERS-active medium so that it has the capability of generating SERS, and the analytical instrument employed will preferably be a Raman spectrometer. In those embodiments, software will be used to verify that the spectrum is of DPA, and to determine the concentration, level of contamination, and present the analysis as appropriate.

Suitable SERS-active sample containers include, but are not limited to, substrates, electrodes, vials, capillaries, and channels contained in a lab-on-a-chip format. The SERS-active medium will comprise at least one SERS-active metal; preferably copper, gold, silver, nickel, or an alloy or mixture thereof will be employed. SERS-active metals can be produced by chemical or electrochemical etching, by photolithographic process, by vapor or chemical deposition, by reduction of metal salts, or other means known to those skilled in the art of performing SERS.

Examples of SERS-active sample containers comprised of SERS-active media include electrochemical cells having SERS-active electrodes; substrates such as a glass flat-coated with vapor-deposited silver or gold directly or on an appropriate SERS-generating structure, such as polystyrene spheres; vials and glass capillaries filled with SERS-active media; microchip devices that include SERS-active channels; and containers of SERS-active colloids.

The specific use of SERS to detect spores also includes the use of SERS-active colloids added to the sample. For example, a SERS-active colloidal solution can be added directly to a surface pretreated with a weak acid, or preferably, a solution of SERS-active colloid in a weak acid can be added directly to a surface. In the foregoing cases, the sample could be drawn through a filter into a sample holder and measured, or a fiber optic probe or Raman microscope could be used to measure the DPA on the surface. As will be appreciated from the forgoing by those skilled in the art, any suitable SERS-active sampling system can be employed to measure DPA obtained from spores.

The Raman spectrometer employed to acquire the SER spectrum may be a dispersive device, a scanning device, an interferometric device, or an acousto-optically tuned device. The software of the apparatus will in any event normally be programmed to determine, from the acquired SER spectrum, if DPA or another analyte chemical is present and, if so, in what concentration or amount. Although any Raman spectrometer, operating with any suitable laser excitation wavelength, can be used in the practice of the invention, an interferometer-based system, having wavenumber stability, will generally be preferred.

DETAILED DESCRIPTION OF THE PREFERRED AND ILLUSTRATED EMBODIMENTS

As indicated above, the present invention provides a novel method and apparatus for effecting the release of a signature chemical from endospores and for detecting it's corresponding analyte chemical. The method and apparatus enable rapid detection, identification and quantitation at room temperature, and the information obtained enables the assessment of risk associated with exposure to bacterial endospores.

Figure 1:
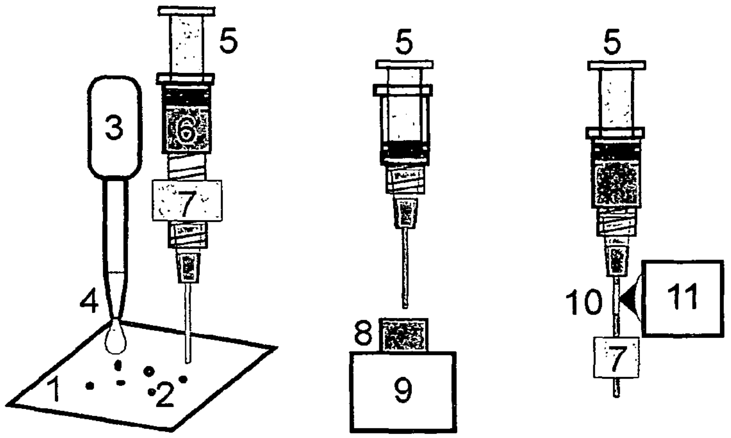
FIG. 1 is a schematic illustration of an apparatus arrangement and procedure suitable for use in carrying out the method of the present invention, consisting of a source of spores (e.g., a surface of mail sorting equipment), a delivery device (e.g., an eyedropper, pipette, or syringe) to deliver a CaDPA releasing chemical, an extraction system (e.g., a syringe with a filter), a SERS-active capillary, and a Raman spectrometer.

An important application for the present method is illustrated in FIG. 1, wherein a surface, designated by the number 1, is analyzed to determine if it is contaminated with *Bacillus anthracis* endospores 2 and, if so, to determine the level of contamination. The surface 1 may for example be that of an automobile, a building window, an office desk, a bin for holding mail, a roller used to move mail through sorting equipment, or the like.

In accordance with the procedure depicted, a pipette 3 is used to dispense a predetermined volume of weak acid 4 onto the surface 1, where it is allowed to interact so as to cause CaDPA to be released from any endospores that might be present into the weak acid liquid; a 10 microliter drop of the acid will typically spread over a 10 $cm^2$ area. If glacial acetic acid is used, most, if not all, of the CaDPA will be released in 1-5 minutes. After waiting for an appropriate period of time, syringe 5 is used to draw the resulting liquid sample mixture (i.e., the product of the acid/endospore interaction) through a filter 7 (to remove any residual spore casings or spore debris) and into the body 6 of the syringe 5. The filter 7 is removed, and the analyte substance (liquid containing DPA) is dispensed into a sample container 8 of an analytical instrument 9.

Alternatively, a swab (not shown) could be used to collect spores from a surface of a predefined area then placed into a small container (also not shown) of the weak acid employed. Then, as previously described, a syringe 5 could be used to collect the sample-containing liquid mixture, for ultimate analysis.

In a preferred embodiment, the sample container 8 is SERS-active and the analytical instrument 9 is a Raman spectrometer. In yet a more preferred embodiment (also shown in FIG. 1), the filter 7 is placed directly ahead of and in liquid flow communication with, a SERS-active capillary 10, so that any spore debris in the sample mixture is removed prior to being drawn into the SERS-active capillary. The capillary is then placed into an appropriate sample holder (not shown) of the Raman spectrometer 11, which locates the SERS-active medium so as to enable the SER spectrum of the analyte substance to be measured and recorded. Computer-driven software, resident in the spectrometer 11, analyzes the spectrum to determine if DPA is present and, if so, in what quantities, and calculates the corresponding number of spores.

The SERS-active capillary is preferably a 1-mm glass capillary filled with a silver-doped sol-gel prepared in accordance with the method described by Farquharson et al. in U.S. Pat. No. 6,623,977, with modification for filling capillaries described by Farquharson et al. (see *Appl Spectrosc* paper, supra). In essence, a silver amine complex, consisting of a 5:1 v/v solution of 1 N $AgNO_3$ and 28% $NH_3OH$, is mixed with an alkoxide consisting of a 2:1 v/v solution of methanol and tetramethyl orthosilicate (TMOS) in a 1:8 v/v silver amine: alkoxide ratio. A 0.15 mL aliquot of the forgoing mixture is drawn into a 1-mm diameter glass capillary to fill a 15-mm length. After sol-gel formation, the incorporated silver ions are reduced with dilute sodium borohydride, followed by a water wash to remove residual reducing agent.

Figure 2:
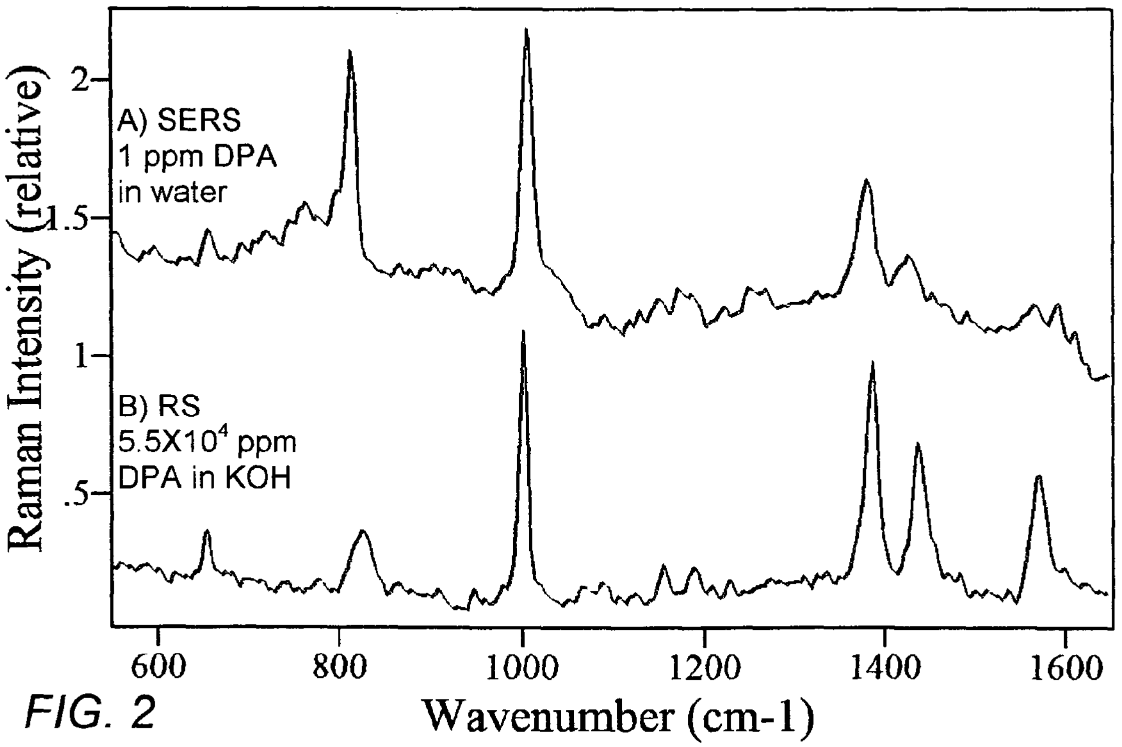
FIG. 2 is a plot of curves showing A) the surface-enhanced Raman spectrum of 1 microgram/mL (equivalent to 1 part-per-million (ppm)) of dipicolinic acid in water contained in a silver-doped sol-gel capillary acquired in one minute using 150 mW of 785 nm laser excitation; and B) the normal Raman spectrum of a 0.33M solution of DPA in 1 N KOH (equivalent to $5.5\times10^4$ ppm) in a plain glass capillary, acquired in 25 minutes using 300 mW of 785 nm laser excitation.
Figure 3:
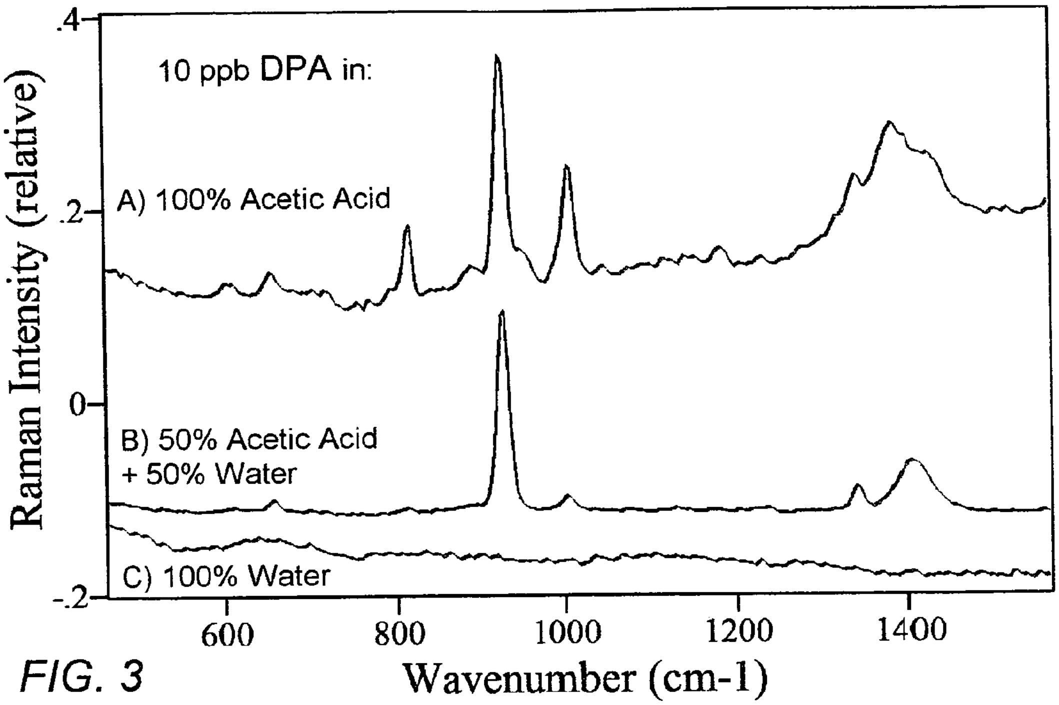
FIG. 3 is a plot of curves showing the surface-enhanced Raman spectra of 10 parts-per-billion (ppb) of dipicolinic acid in A) glacial acetic acid, B) in 50% acetic acid and 50% water, and C) in 100% water, all collected in SERS-active glass capillaries using 85 mW of 785 nm laser excitation and 1 minute acquisition time.

As indicated in FIG. 2A, DPA produces a unique SER spectrum, consisting of major peaks at 657, 815, 1008, 1382, 1428, and 1567 $cm^{-1}$, which can therefore be used to show its presence. It can also be seen by comparison in FIG. 2B, that the SERS signal intensity of a 1 part-per-million DPA sample in water is equivalent to the normal Raman signal intensity of a 5.5% ($5.5\times10^4$ ppm) solution of DPA in 1N potassium hydroxide. DPA is only slightly soluble in water, and a basic pH solution is required to dissolve significant quantities. Since the latter spectrum was acquired using twice the laser power, the DPA signal is enhanced by $1.1\times10^5$, which is representative of the SERS effect. It is important to note that the SERS measurement of DPA is substantially improved when acetic acid is used as the solvent. At 10 ppb, DPA is generally not observed in water (FIG. 3C), but quite pronounced in acetic acid, as shown in FIG. 3A, albeit, as shown in FIG. 3B, at least a 50% concentration of acetic acid in water is generally required.

Figure 4:
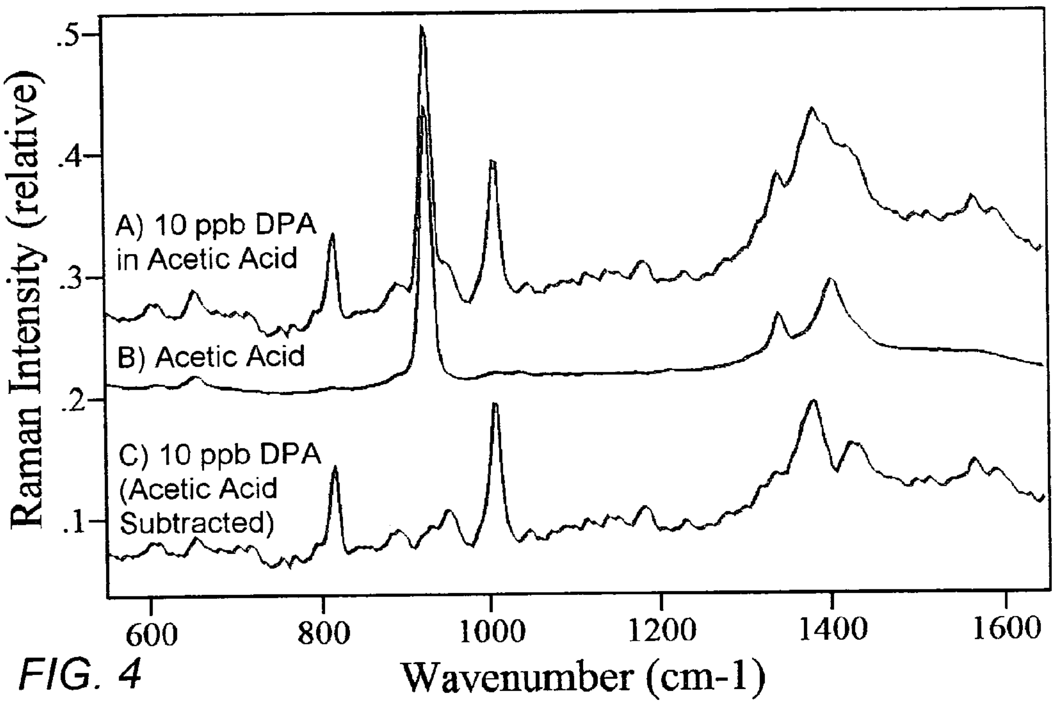
FIG. 4 is a plot of curves showing the surface-enhanced Raman spectra of A) 10 ppb of dipicolinic acid in glacial acetic acid, B) glacial acetic acid alone, and C) 10 ppb of dipicolinic acid obtained by subtracting curve B) from curve A); spectral acquisition conditions are as in FIG. 3.

The DPA/acetic acid spectrum also contains an intense peak at 925 $cm^{-1}$ and minor peaks at 1340 and 1405 $cm^{-1}$ due to acetic acid. A reference spectrum of acetic acid can be subtracted from the sample spectrum to remove these peaks, as shown in FIG. 4, or they can be left in the spectrum as an internal spectral intensity standard.

The intensity of the DPA SERS signal scales with concentration. This is demonstrated by showing four orders of magnitude of DPA concentration shown in FIG. 5, in which the dominant DPA signal is held constant and the base line noise is observed to increase with decreasing concentration. Previous SERS measurements, made using known amounts of DPA, can be employed to calibrate the response of the SERS-active media and the Raman spectrometer to quantify the amount of DPA in terms of the number of spores in the sample. The calculation utilized is based upon the fact that each endospore has an approximate mass of 10 picograms and contains on average 10 wt % CaDPA.

Figure 6:
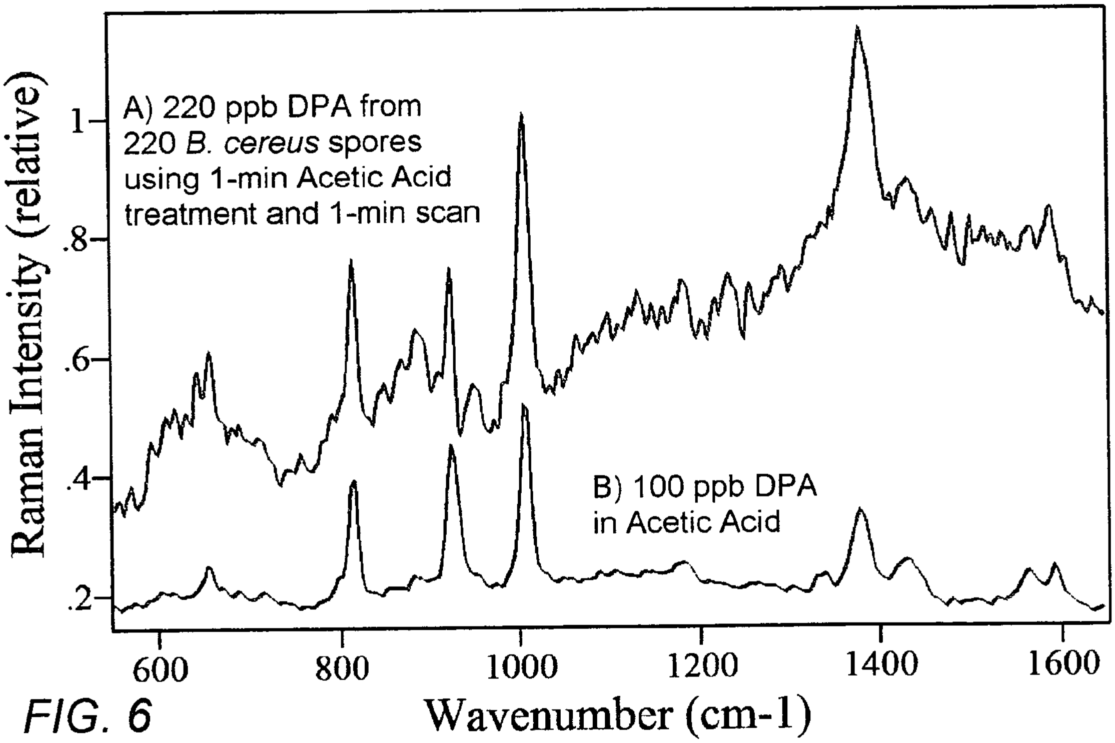
FIG. 6 is a plot of curves showing the surface-enhanced Raman spectra of A) DPA obtained from 220 *Bacillus cereus* spores using a 1-minute exposure to glacial acetic acid, and B) 100 ppb DPA in glacial acetic acid for comparison; spectral acquisition conditions are as in FIG. 3.

The measurement of actual spores on a surface described above has been performed, as follows: A sample of 2200 *Bacillus cereus* spores was deposited on a glass slide from a calibrated solution of 2200±200 spores per microliter of water. Once dried, this represented an analyte sample of spores. Ten microliters of glacial acetic acid was added to the spore sample, and allowed to cause CaDPA to be released at room temperature for 1 minute. A 1-microliter aliquot of the resultant mixture, containing the DPA from an estimated 220 spores, was drawn into a SERS-active capillary, by syringe. The capillary was placed in a sample holder of a Raman spectrometer, and a 1-minute spectrum was recorded using 85 mW of 785 nm laser power as shown in FIG. 6A. If 10 wt % DPA was obtained from these spores, then the measured spectrum is indicative of a concentration of 220 parts-per-billion, which is in reasonable agreement with the 100 ppb reference spectrum shown in FIG. 6B for comparison. Here, the acetic acid peak at 925 $cm^{-1}$ can be used as a frequency standard or, more importantly, as an internal intensity standard, and when the two spectra are scaled so that the acetic acid peak has the same intensity, then the relative intensity of the spore sample can be compared to the 100 ppb reference. In doing so, the measured spectrum suggests that the sample contained 180 ppb DPA. This value compares favorably with the estimated 220 ppb value, since it was based on spores containing 10 wt % DPA, which could in fact have been slightly lower.

Figure 7:
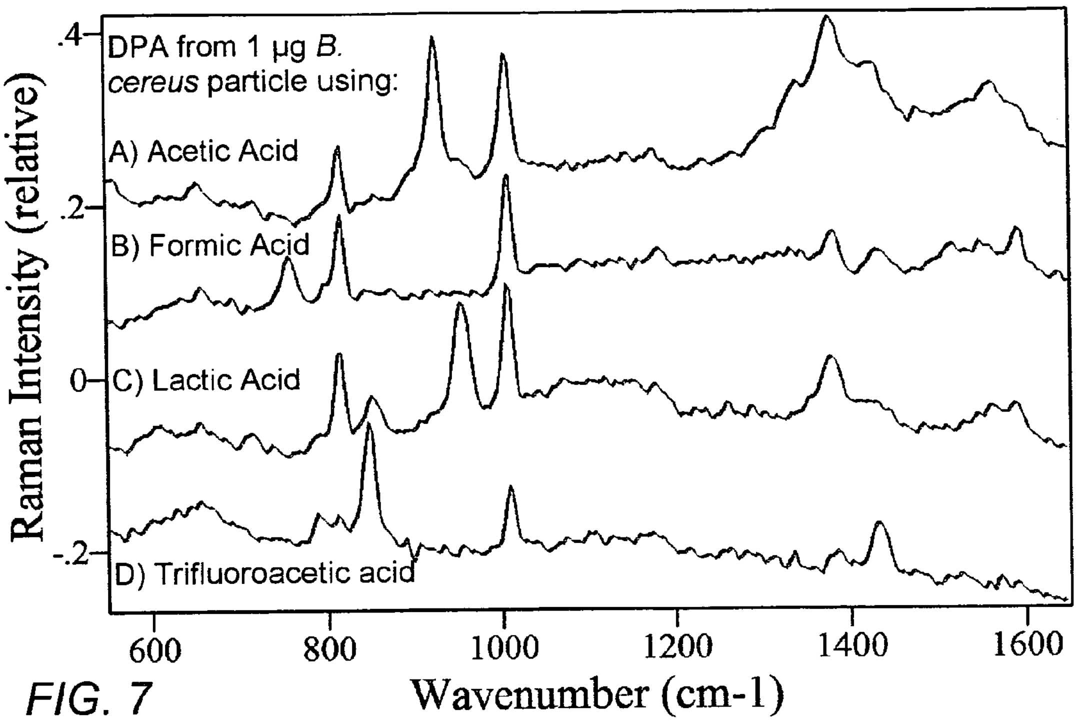
FIG. 7 is a plot of curves showing the surface-enhanced Raman spectra of DPA obtained from 10 microgram particles of *Bacillus cereus* spores using a 1-minute exposure to A) glacial acetic acid, B) formic acid, C) lactic acid, and D) trifluoroacetic acid; spectral acquisition conditions are as in FIG. 3.

Acetic acid is not the only weak acid that will cause CaDPA to be released at room temperature. The SERS of DPA was also observed when formic acid, lactic acid and trifluoroacetic acid were each individually added to 10 microgram particles of *B. cereus* spores as shown in FIG. 7. In each case, the spore particle was exposed to the weak acid for 5 minutes, and then a 1-minute spectrum was acquired using 85 mW of 785 nm. Each weak acid also generated additional peaks in the spectrum, specifically at 755, 855 and 955, and 845 $cm^{-1}$ for formic acid, lactic acid and trifluoroacetic acid, respectively. The spectra were in general not as sensitive as that obtained when the identical experiment was performed using acetic acid. Of course, improvements in sensitivity could be made by using an acidic composition consisting of one or more weak acids at various concentrations using various solvents.

Figure 8:
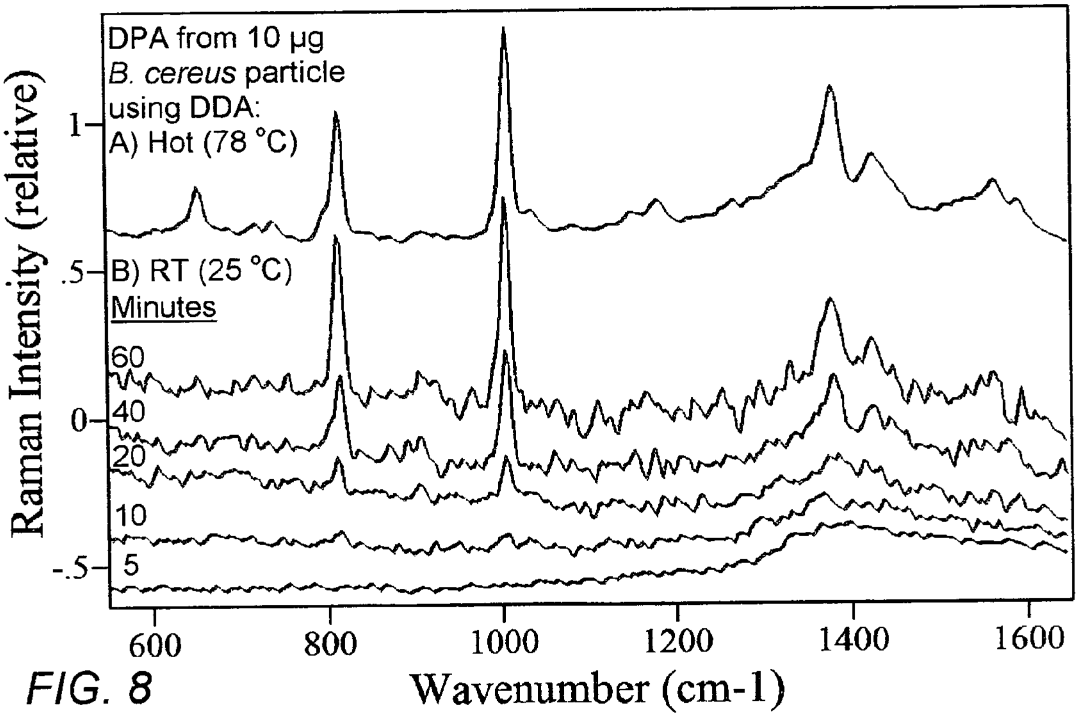
FIG. 8 is a plot of curves showing the surface-enhanced Raman spectra of A) DPA obtained from 10 microgram particles of *Bacillus cereus* spores using A) a 1 minute exposure to hot (78° C.) dodecylamine, and B) a series of exposures (5, 10, 20, 40, and 60 minutes) to room temperature dodecylamine; spectral acquisition conditions are as in FIG. 3.

The ability to cause CaDPA to be released at room temperature, so that DPA can be measured by SERS, simplifies measurements by eliminating the need for equipment that has heretofore been required to heat the release agent and/or to break apart the spores by ultrasound, as previously described. In one case (see the Farquharson et al. *Appl Spectrosc* paper, supra), dodecylamine was used to cause, in some fashion, CaDPA to be released. SERS measurements of a 10 microgram spore sample in a 50 mM solution of DDA required 1 hour exposure at room temperature before a reasonable DPA SERS signal was observed, which even then was substantially weaker than that obtained using a 1 minute exposure of DDA heated to 78° C., as shown in FIG. 8. Even in the case of hot DDA, the measured amount reported was 10,000 spores per microliter sample; i.e., the measurement was considerably less sensitive than that shown in Figure of the 220 spores per microliter sample.

Figure 9:
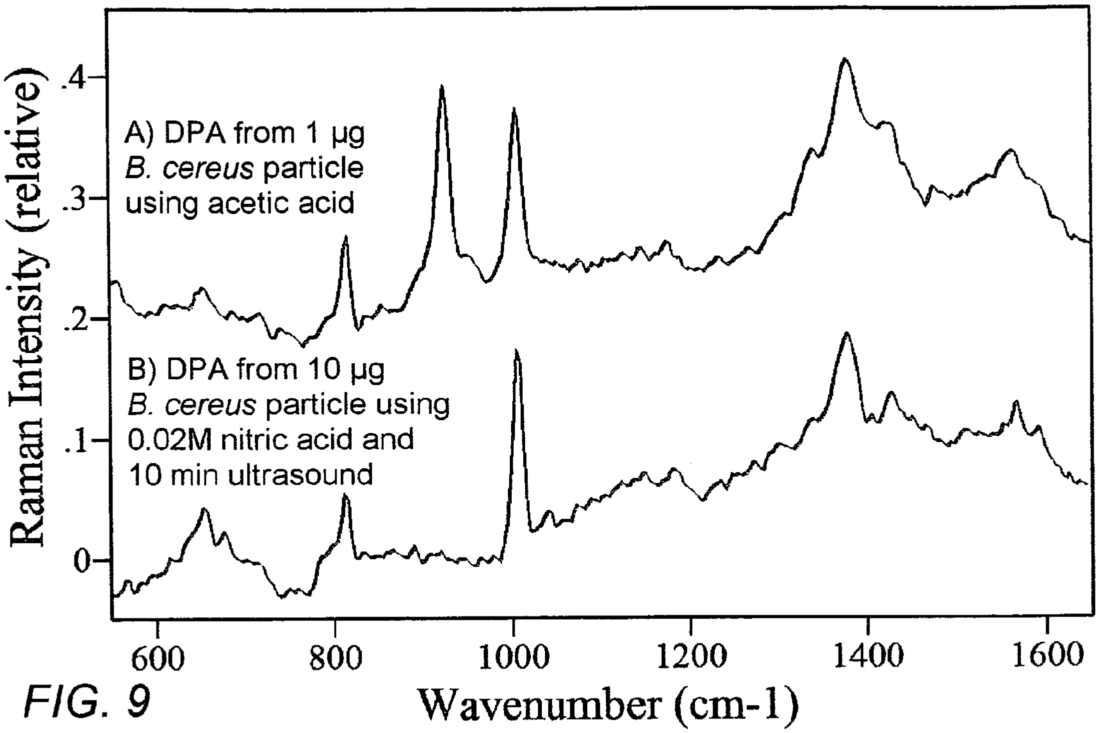
FIG. 9 is a plot of curves showing the surface-enhanced Raman spectra of A) DPA obtained from A) a 1 microgram particle of *Bacillus cereus* spores using a 1 minute exposure to glacial acetic acid, and B) a 10 microgram particle of *Bacillus cereus* spores using a 10-minute exposure to 0.02M nitric acid and sonication; spectral acquisition conditions are as in FIG. 3.

In another case (see the Zhang et al. paper, supra), 0.02 M nitric acid was used in conjunction with 10 minutes of ultrasonification to obtain a SER spectrum of DPA. However, the lowest reported amount measured was 187,000 spores per microliter. FIG. 9 compares the SERS of a 1 microgram spore sample obtained using acetic acid at room temperature to the SERS of a 10 microgram spore sample obtained using 0.02 M nitric acid and 10 minutes of ultrasonification. Both samples were recorded using identical SERS-active capillaries, and the same Raman spectrometer and measurement conditions. As can be seen, the noise and background of the latter spectrum is substantially higher, suggesting spectral contributions and interference due to spore cell debris.

In another demonstration of the broad applicability of the present invention, a sample of spores artificially added to saliva was measured. In this case, a 50 microgram sample of *B. cereus* spores was dispersed into 1 mL of water (5000 spores per microliter). A 1 microliter of this sample was thoroughly mixed with a 9 microliter sample of saliva to effectively produce a sample of 50 nanograms of spores per 10 microliter of saliva. To this sample, 10 microliters of glacial acetic acid was added to produce a sample of 2.5 nanograms per microliter of solution (250 spores per microliter). After allowing the acetic acid to cause the CaDPA to be released for 1 minute at room temperature, 1 microliter of the mixture was drawn into a SERS-active capillary by syringe. Then, just as described previously for FIG. 6, and shown here in FIG. 10A, the SER spectrum was recorded and used to calculate that the measured sample contained 235 ppb of DPA, i.e., a value very close to the expected 250 ppb of DPA.

Figure 10:
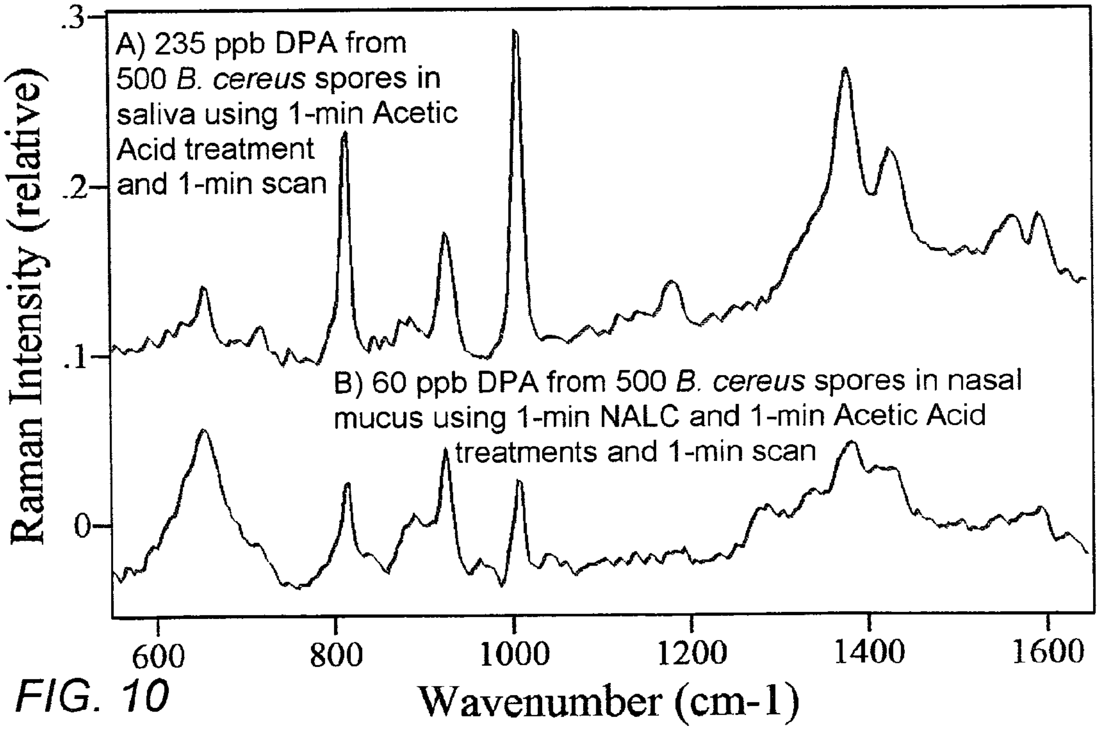
FIG. 10 is a plot of curves showing the surface-enhanced Raman spectra of DPA obtained from 500 *Bacillus cereus* spores in A) saliva using a 1-minute exposure to glacial acetic acid, and in B) nasal mucus using 1-minute exposures to first 1 M NALC then glacial acetic acid; spectral acquisition conditions are as in FIG. 3.

In yet another demonstration of the broad applicability of the present invention, a sample of spores artificially added to nasal mucus was measured. The identical experiment described above was performed, and no DPA SERS signal was observed. However, if the sample of 50 nanograms of spores per 10 microliter nasal mucus was first treated with an equivalent amount of 1M NALC for 1 minute, the mucus immediately lost its viscosity, signifying its chemical degradation. This sample was further treated with 10 microliters of glacial acetic acid, releasing the CaDPA such that DPA could be detected by SERS as shown in FIG. 10B. Here the relative DPA and acetic acid peak intensities suggest that the spectrum is of 60 ppb DPA. This is consistent with the additional dilution of the sample by NALC. It is also worth noting that NALC does produce a SER spectrum, with relatively intense peaks at 660 and 890 $cm^{-1}$. Fortunately, these peaks do not overlap with the primary DPA peaks at 815 and 1008 $cm^{-1}$, and hence do not interfere with the measurement.

As a still further example of the broad applicability of the present invention, sample container 8 may alternatively contain a solution of terbium ions that can complex with the DPA, and the analytical instrument may be a fluorescence spectrometer that can be used to generate and measure the photoluminescent spectrum of the sample. Quantitative analysis can be performed much like that described for the SERS measurements.

In yet another embodiment, the sample container is the entry point of an assay that contains a metal complex with a dye that, if reacted with DPA, produces a color change that can be seen by the unaided eye. Although such measurements are improved by the present invention, the limitations of photoluminescence and assay measurements, previously described, remain.

Figure 11:
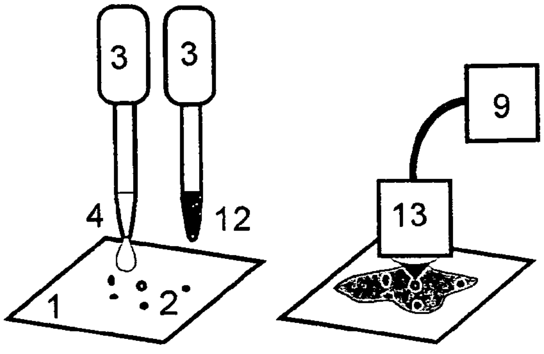
FIG. 11 is a schematic illustration of a second apparatus arrangement and procedure suitable for practicing the present invention, consisting of a site for endospores (a contaminated surface); a delivery device (e.g., an eyedropper, pipette, or syringe) to deliver a CaDPA releasing chemical; a second delivery device to deliver a DPA indicator solution, such as a SERS-active colloid; a fiber optic probe; and an analytical instrument.

An alternative procedure and apparatus arrangement, which is suitable for use to determine if a surface is contaminated with anthrax spores, is shown in FIG. 11 (elements bearing common reference numbers are the same as, or equivalent to, elements elsewhere referred to). As previously described, a first pipette 3 is employed to dispense a drop of a weak acid 4 onto the sample surface 1. After the appropriate time, typically 1-5 minutes, a DPA indicator solution 12 is added to the surface 1 from a second pipette 3. A portable analytical instrument 9 is then used to detect, identify, and quantify the DPA, and hence the amount of spores present on the surface. The analytical instrument may have an optical interface 13 that allows mapping (point-by-point analysis) or imaging of the surface. The optical interface could be an imaging camera or a fiber optic probe. In a preferred embodiment, the indicator solution is a SERS-active silver colloid, and the analytical instrument is a Raman spectrometer with a fiber optic probe and mapping stage; computer-driven software again performs the analysis of DPA, as described. As a further example of the broad applicability of the present invention, the indicator solution could be a terbium or dye complexing solution, and the analytical instrument could be a fluorescent spectrometer or, indeed, the unaided eye.

Figure 12:
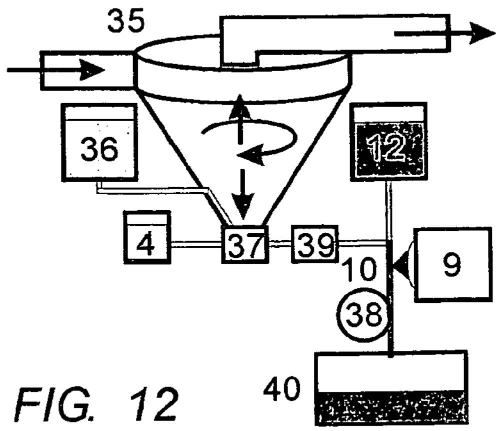
FIG. 12 is a schematic illustration of another arrangement of apparatus and procedure suitable for use in the present method, consisting of an endospore collector and concentrator (e.g., a wet-walled cyclone), a reservoir of a weak acid solution, a collection system, a pump and filtering system, a reservoir of a DPA indicator solution, such as SERS-active metal colloids, and an analytical instrument, such as a Raman spectrometer.

Yet another example of an application in which the method of the present invention can be used to measure DPA, in accordance with the present invention, involves the assessment of airborne spores, as depicted diagrammatically in FIG. 12. A device, designated by the number 35 and advantageously taking the form of a cyclone unit, is used to collect airborne particulate matter. The device is comprised of a conical enclosure, through which large volumes of air are drawn at substantial speeds and which employs induced air-flow patterns and centrifugal and gravitational forces to separate and deposit particles into a collector 37. The shape and size of the cyclone, and the air velocities employed, can be such that it (or series of such devices) can be used to separate and collect particles of a selected size range from a predefined volume of air moving at a predefined flow rate; in the case of *Bacillus* and *Clostridium* spores, the device should be capable of separating particles of 1-20 microns. The separated particles are introduced into a solution 4 that is capable of interacting therewith so as to release DPA, as previously described.

Rather than using a syringe 5 to draw a sample through a filter 7 into a SERS-active media 8, as previously described, a solution can be caused to wash the inner wall surfaces of the device 35 so as to carry the deposited particles into the collection chamber 37. A pump 38 can be operated to effect admixture of the analyte solution, so produced, with a weak acid solution 4, and to then pass the admixture through a filter (as hereinabove described) or a filter tape 39, for effecting removal of the cell component debris.

The device may advantageously use a weak acid as the wall-washing solution 36. In either event, the DPA-containing solution would pass the measurement point of an analytical instrument 9 and be measured in the usual way, prior to discharge to a waste container 40. Alternatively, the pump 38 could be employed to simultaneously draw a DPA indicator solution 12, into the tubing that carries the DPA solution, and to effect mixing of the two components so that the mixture passes the measurement point of an analytical instrument. Irrespective of whether the DPA solution is caused to combine with an indicator solution 12 prior to passing an analytical instrument measurement point or simply flow past the measurement point, the analysis for the presence of DPA, and hence for endospores, can be performed continuously.

In the foregoing cases, either the measurement point could contain a SERS-active medium 10, or the DPA indicator solution 12 could be a flowable SERS-active medium (e.g., a silver or gold colloid). In either case the analytical instrument would be a Raman spectrometer. It will be appreciated by those skilled in the art of measuring airborne particulate matter that other collection devices, such as impactors, can of course be used to a similar effect.

It will of course also be appreciated by those skilled in the art that, despite being acquired continuously (as may be necessary or desirable), the reporting of data may occur at intervals of seconds or minutes, or even hourly, as appropriate. It will also be appreciated that various combinations and modifications of the described techniques and apparatus can of course be employed without departure from the concept and scope of the present invention.

Figure 13:
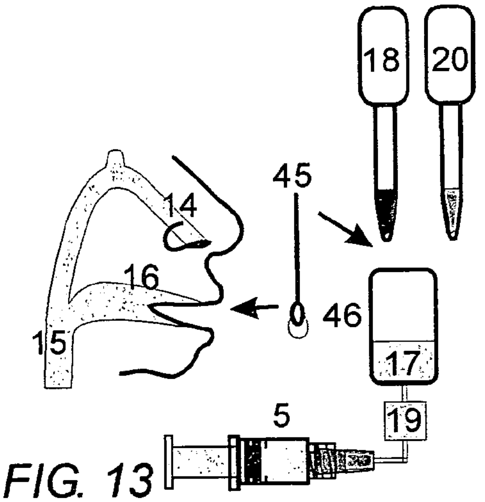
FIG. 13 is a schematic illustration of another alternative form of apparatus and procedure, which would be used with the apparatus arrangements of the preceding figures, consisting of a source of endospores (nasal passage, throat or mouth), a swab to collect endospores, an eyedropper or pipette to deliver a mucus-liquefying agent (e.g. NALC) to the sample, a filter to collect spores and pass the liquefied mucus, a solvent to wash the collected spores.

In another important application, FIG. 13 illustrates the method of the invention used to determine if a person has been exposed to anthrax-causing spores. As depicted, a swab 45 is used to withdraw mucus, sputum, or saliva from the nasal passage 14, throat 15, or mouth 16 of the subject, which are of course the natural sites for the deposit of spores and therefore for the collection of samples; alternatively a sample could be expelled directly into a vessel 46, or the collection cavity or site could be flushed with a predetermined volume of solution and collected in the vessel 46. In any event, the sample matrix or carrier 17, suspected of containing spores, will consist of mucus, sputum or saliva, as the case may be, and appropriate weightings will of course be carried out to determine the amount of sample employed in each instance.

To prepare a mucus-containing sample, an equal volume of a mucin-liquefying solution 18, such as a mucolytic agent consisting of 1% N-acetyl-L-cysteine with 5% NaOH, is added to the sample 17 in vessel 46 (FIG. 13). Once the mucins are liquefied, the sample is drawn or pushed through a filter 19, which passes the liquefied mucins and other small molecules, while retaining the spores. A solvent 20, such as 50/50 v/v methanol/water solution, is then drawn through the filter 19, as needed to remove residual chemicals from the spores. As discussed above in connection with FIG. 1, the filter and retained spores may then be placed into vessel 46 containing a predetermined volume of a weak acid solution that is capable of interacting with the endospores and releasing DPA; or as discussed in regard to FIG. 11, pipettes 3 may be used to dispense drops of weak acid solution, and a DPA indicator solution 12 so that the sample can ultimately be analyzed. It will also be recognized by those skilled in the art of chemical and biological separations that, in conjunction with the filter or membrane 19, additional separation materials, such as pre-concentrating or ion exchange materials, could advantageously be used to improve separation of the spores and/or the DPA.

Figure 14:
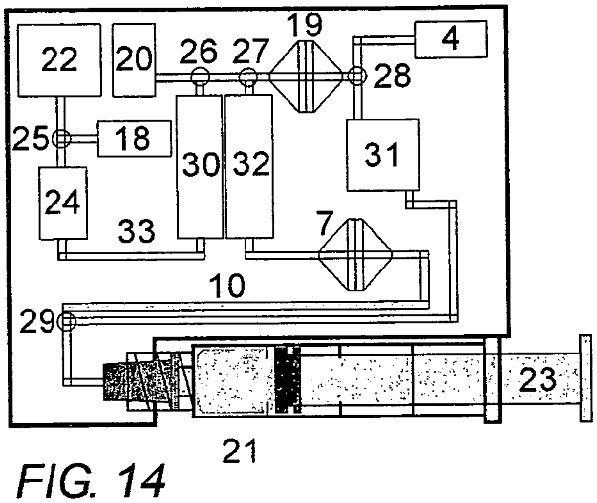
FIG. 14 is a schematic illustration of yet another form of apparatus and procedure suitable for use in practicing the invention, consisting of a lab-on-a-chip device containing reagents or a reagent supply, channels, valves, mixing chambers, filters, and a flow control system to separate spores from mucus, to mix a weak acid with the spores so as to effect the release of CaDPA, and to deliver DPA to the measurement point of an analytical instrument, preferably an integral SERS-active channel to be used in conjunction with a Raman spectrometer.

In a further illustrated embodiment of the invention, the method of the invention is carried out using the lab-on-a-chip device depicted in FIG. 14. In using the device, the mucin, sputum or saliva sample 17 (not shown in FIG. 14) suspected of containing endospores is introduced at a sample entry point 22, and a syringe 23, or similar device, is used to draw the sample into a load chamber 24 of predefined volume (such an arrangement could also be constructed to use positive pressure for liquid transport). By selectively opening and closing valves 25-29, to appropriately connect chambers by microchannels 33, a predefined volume of a mucan-liquefying chemical 18 is drawn through the load chamber 24 and with the sample into a mixing chamber 30; the valves can be operated automatically using electronic, magnetic, or pneumatic means, or manually. The necessary mixing can be achieved by means of channel design and/or by reciprocation of the syringe plunger so as to cause the sample to flow back and forth through and within the mixing chamber.

By appropriately changing the valve positions and operating the syringe plunger, the sample, now composed of endospores in a liquefied mucin matrix, is drawn through a filter or membrane 19, which is constructed to pass the liquefied mucins and other small molecules while retaining the spores, and is thereafter discharged into a waste chamber 31. Again by appropriate settings of the values and operation of the syringe, a solvent 20 is drawn over the spores through the filter or membrane 19, as needed to remove residual chemicals, following which a predetermined volume of weak acid 4 is drawn through the filter or membrane 19, in a reverse-flow mode, so as to carry the spores into a second mixing chamber 32. Again using the syringe and the valves set at appropriate positions, the DPA thus released from the spores is drawn through a second filter 7, which passes the DPA to the measurement point of an analytical instrument 9. In the case of performing SERS, the measurement point would preferably be a SERS-active capillary 10, the SER spectrum would be measured by a Raman spectrometer, and the analysis would be performed as previously.

Exemplary of the efficacy of the method of the invention are the following specific examples:

EXAMPLE 1

Analysis of a Mail Sorter for Anthrax-Causing Endospores

Figure 5:
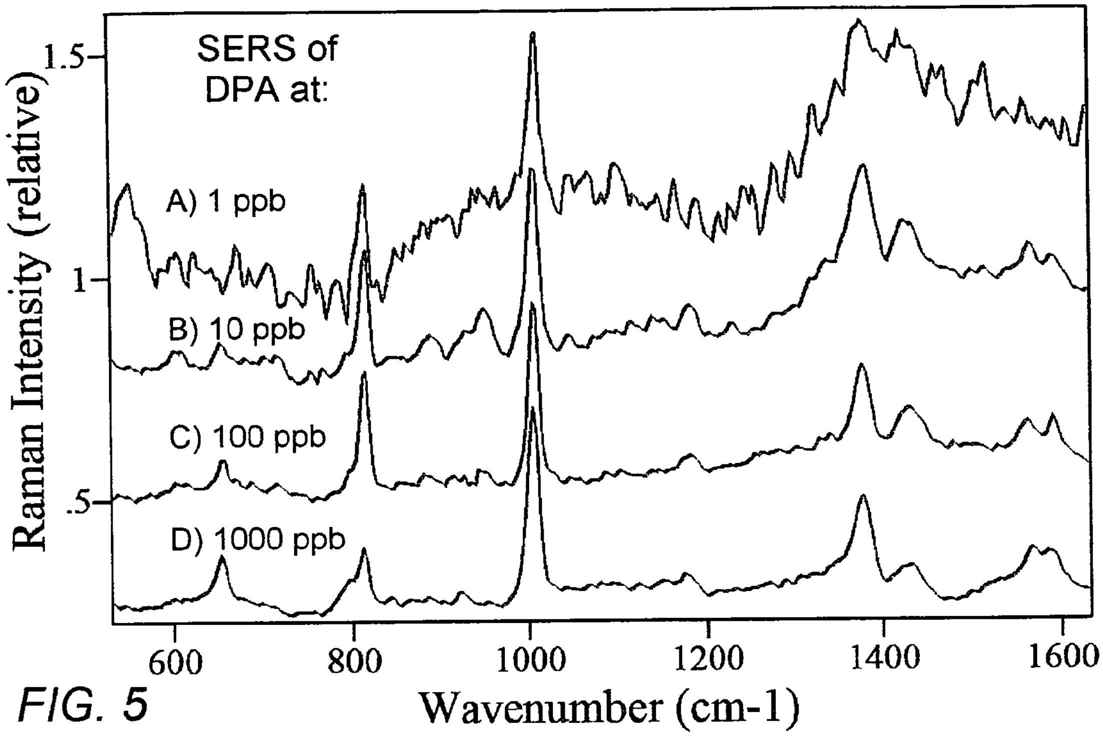
FIG. 5 is a plot of curves showing the surface-enhanced Raman spectra of A) 1, B) 10, C) 100, and D) 1000 ppb of dipicolinic acid (the glacial acetic acid spectrum having been subtracted); spectral acquisition conditions are as in FIG. 3.

An envelope containing 1 g of *Bacillus anthracis* spores is passed through a mail sorting machine, hypothetically leaving behind an average of 100 picograms, or 10 spores per $cm^2$ (invisible to the unaided eye), on the equipment surfaces 1. With reference to FIG. 1, 50 microL of glacial acetic acid is dispensed onto the surface, which spreads over a 100 $cm^2$ circular area of the machine. During the course of 1 minute, the acetic acid effects the release of CaDPA from the estimated 1000 spores, producing from 0.5 to 1.5 nanograms of DPA in the solution. A 1 mL syringe 5 is used to draw 10 microliters of the acetic acid solution 6, containing on average 0.2 ng of DPA, through a PTFE filter 7 into a 1-mm diameter glass capillary containing a SERS-active sol-gel 10. The capillary is then mounted in the sample holder of a Raman spectrometer 11, and 85 mW of 785 nm laser excitation radiation is focused into the silver-doped sol-gel; the surface-enhanced Raman spectral radiation, so generated, is collected. Computer-driven software produces, from the collected radiation, a spectrum similar to that shown in FIG. 6. The peaks observed at 657, 815, 1008, and 1382 $cm^{-1}$ are sufficiently unique to confirm that DPA is present, and the intensity of the peak at 1008 $cm^{-1}$ allows calculating that DPA is present at a concentration of 20±10 ng per 1 mL solution. It is worth noting that 10 ng/mL (10 ppb) DPA in acetic acid can routinely be measured using the instant method, as shown in FIG. 4. The error in the measurement is of course due to the variability of the amount of CaDPA contained in any given spore (5-15 wt %). Previous measurements of multiple samples allows construction of a calibration curve that relates the 1008 $cm^{-1}$ peak intensity to known concentrations, such as is shown in FIG. 5(A-D). The calculated value obtained further indicates that the surface was contaminated by 1000±500 spores.

EXAMPLE 2

Continuous Analysis of Air to Detect *B. anthracis* Endospores

A container of *B. anthracis* endospores is opened and left in the lobby of a commercial building, causing the release of 20,000 spores per cubic meter of air. Ambient air is drawn into a return duct of the building ventilation system, and is passed, at the rate of one cubic meter per minute, through a large-particle filter or large-particle cyclone-separator, and (with reference to FIG. 12) into a cyclone unit 35. The cyclone is designed to retain particles of 1-5 micron in collector 37 while passing particulate matter of finer sizes. A thin film of acetic acid is caused to flow from the reservoir 36 over the inner, lower portion of the conical enclosure of the cyclone, thereby collecting 50 percent of the deposited particles; air is passed through the cyclone at the rate of one cubic meter per minute, and acetic acid is collected at the rate of 50 mL per minute. A pump 38, and appropriate valves (not shown), are used to empty the collector 37 every minute and to pass the particulate-containing wash acetic acid through a filter tape 39, which traps the spore components and passes the DPA, following which the purified DPA is mixed with 10 mL of a silver colloid as the DPA indicator solution 12, and the admixture is caused to flow past the measurement point of the Raman spectrometer as the analytical instrument 9 and thereafter into a waste container 40. The Raman spectrometer measures the SER spectrum of the entire stream of sample (the volume of which is slightly greater than one liter), and determines the amount of spores contained in each cubic meter of air sampled, which is found in this example to be about 20,000 spores. The apparatus interfaces to an alarm system (not shown), and produces an audible or visual signal, as appropriate.

It is of course appreciated that, in the foregoing example, a terbium complexing agent could be used in place of the silver colloids, and of course then a fluorescence spectrometer would be used in place of the Raman spectrometer.

EXAMPLE 3

Analysis of Hospital Air for *Clostridia* Endospores

*Clostridia* are one of the most common bacterial causes of food-borne illnesses (*Clostridium perfengens*), including botulism (*Clostridium botulinum*). They also cause tetanus (*Clostridium tetani*), pseudomembranous colitis, and antibiotic associated diarrhea, the latter being the most frequently identified cause of hospital-acquired diarrhea (*Clostridium defficile*). For example, see McDonald L C, M Owings, D B Jernigan, "Increasing Rates of *Clostridium difficile* Infection Among Patients Discharged from US Short-Stay Hospitals, 1996-2003", *Emerg Infect Dis,* 12, 1-20, 2006.

Similar to the previous Example, the ambient air is drawn into a return duct of a hospital ventilation system, and is passed, at the rate of one cubic meter per minute, through a multi-stage impactor that captures particles of decreasing size range as it passes through each stage, until finally, particles of 1-5 micron are deposited into numerous vials residing on a carousel that rotates such that each vial collects a predefined portion of particles sequentially at a predefined rate. The vials contain glacial acetic acid, and the inner wall is coated with a SERS-active metal doped sol-gel. After a sample of particles is collected the vial moves in a step-wise fashion from the sample collection point to a Raman spectrometer measurement point. SERS of the sample is collected and analyzed in the usual way. The apparatus interfaces to an appropriate system to warn hospital personnel when airborne clostridium endospore concentrations are too high, as appropriate.

EXAMPLE 4

Analysis for Anthrax-Causing Endospores in Nasal Swabs

It is assumed that a person has been exposed to 5000 *Bacillus anthracis* spores, half of which have been trapped in the mucus of his or her nasal passage. With reference to FIG. 13, a polyester swab 45 is used to collect mucus from the subject's nasal passage 14, and is inserted into the sample entry point 22 of a lab-on-a-chip device 21. The chip is designed for mounting on a portable Raman spectrometer 11, in automatic alignment with magnetic control valves and one or more optical components (such as a lens). A reagent cartridge (not shown) attached to the top surface of the device 21, delivers the appropriate reagents, and interface tubing (also not shown) provides additional flow control valves, as required. A computer program serves to control the entire sequence of valve action and liquid flow.

More particularly, a device such as syringe 23 initially draws the sample into a 50 microL load chamber 24 of the chip device 21, following which 50 microL of a solution 18 of 1% NALC and 5% NaOH is drawn from the reagent cartridge into the loaded sample, carrying it into a 100 microL mixing chamber 30. The syringe plunger is reciprocated so as to mix the sample and "liquify" the mucins, after which the syringe 23 serves to draw the sample through a membrane filter 19 having a pore size of 0.75 micron, which passes the liquefied mucins (into a waste container 31) while retaining the spores. A 50 microL volume of a 50/50 v/v methanol/water solvent 20 is then drawn from the reagent cartridge to pass over the spores and thereby remove residual mucin components. Then, 100 microL of a solution 4 of glacial acetic acid is drawn from the reagent cartridge through the filter 19, in a reverse-flow mode, so as to carry the spores into a second 100 microL mixing chamber 32. The syringe plunger is again reciprocated to effect mixing of the sample, causing the release of (on average) 10 wt % (1-1.5 ng) of DPA. The syringe is then operated to draw the sample through a section of the microchannel 33 filter 7 consisting of tubing packed with SHODEX 7 filtering material, passing the DPA while retaining the endospore debris. Finally, after drawing the DPA into a SERS-active capillary 10, the SER spectrum is obtained and analyzed. The result indicates that the subject was exposed to 5000±1000 spores.

Thus it can be seen that the present invention provides a novel method for rapidly obtaining information to aid in the assessment of health risks associated with exposure to endospores. More specifically, the invention provides such a method wherein a signature chemical, such as in particular calcium dipicolinate (CaDPA), is released from endospores in an analytically detectable form, such as in particular in the form of dipicolinic acid (DPA). Furthermore, the invention provides a novel method in which one or more weak acids is employed to release the signature chemical from the endospores, and in which additional physical means, such as heat or sonication, are not required to ensure release of the signature chemical in a timely manner, e.g., within 10 minutes.

Having thus described the invention, what is claimed is:

1. A method for effecting the release of an analytically detectable form of a signature chemical contained in bacterial endospores, comprising the steps: obtaining a sample comprised of at least one species of bacteria having endospores containing a signature chemical; combining, with at least a component of said sample containing said bacteria, an effective amount of an acidic composition providing, in solution, at least one weak carboxylic acid compound having a dissociation constant of 0.1 to 11, expressed as its pKa value, so as to produce a liquid mixture; and allowing said weak carboxylic acid compound to interact with said endospores for a period of time and under conditions sufficient to effect release from said endospores of an analytically detectable form of said signature chemical as an analyte chemical, to thereby produce an analyte substance containing said analyte chemical.

2. The method of claim 1 wherein said species of bacteria is of the genera *Bacillus* or *Clostridium.*

3. The method of claim 2 wherein said species of bacterial spores is *Bacillus anthracis.*

4. The method of claim 1 wherein said signature chemical is itself analytically detectable, and provides said analyte chemical.

5. The method of claim 1 wherein said signature chemical is selected from the group consisting of calcium dipicolinate, n-acetyl-glucosamine, dipicolinic acid, monoprotonated dipicolinic acid, deprotonated dipicolinic acid, deoxyribonucleic, diaminopimelic, n-acetyl-muramic, ribonucleic, phosphoglyceric, teichoic, and sulfoactic acids.

6. The method of claim 1 wherein said acidic composition is a solvent solution containing about 0.5 to 95 weight percent of an ingredient that produces said weak acid compound.

7. The method of claim 6 wherein the solvent of said solvent solution is selected from the group consisting of acetone, acetonitrile, benzene, chloroform, carbon tetrachloride, cyclohexane, dichloromethane, diethyl ether, dimethylsulfoxide, ethanol, ethyl acetate, ethylene glycol, isopropyl ether, methanol, methyl ethyl ketone, n-hexane, tetrahydrofuran, toluene, water and mixtures thereof.

8. The method of claim 1 wherein said at least one weak acid compound is a $C_1$ through $C_{16}$ acid.

9. The method of claim 1 wherein said at least one weak acid compound is selected from the group consisting of acetic, adipic, citric, formic, fumaric, lactic, malic, palmitic, propionic, salicylic, sorbic, succinic, and trihaloacetic acids, and mixtures thereof.

10. The method of claim 9 wherein said at least one weak acid compound is acetic acid.

11. The method of claim 1 wherein said liquid mixture contains said weak acid compound in a concentration of at least 10 percent by weight of said liquid mixture.

12. The method of claim 1 wherein said step of interacting for releasing said analyte chemical is effected at ambient temperature.

13. The method of claim 12 wherein said ambient temperature is in the range 20° to 25° Centigrade.

14. The method of claim 1 wherein said step of interacting for releasing said analyte chemical is effected at a temperature mildly elevated above ambient.

15. The method of claim 14 wherein said mildly elevated temperature is not above 50° Centigrade.

16. The method of claim 1 wherein said period of time of interaction of said weak acid with said endospores does not exceed 30 minutes.

17. The method of claim 16 wherein said period of time is from 10 seconds to 10 minutes.

18. The method of claim 17 wherein said period of time is 20 seconds to 1 minute.

19. The method of claim 1 wherein said sample comprised of at least one species of bacteria is obtained from ambient air, water, food, a physical surface, or the body of an animal.

20. The method of claim 19 wherein said sample is a human body fluid selected from the group consisting of nasal mucus, throat sputum, saliva and sweat.

21. The method of claim 20 additionally including a step of separating said bacteria from other components of said body fluid to provide said at least a component of said sample containing said bacteria.

22. The method of claim 21 wherein the additional step of separating said bacteria from other components of said body fluid is performed by admixing with said body fluid a degrading chemical selected from the group consisting of mucolytic agents, surfactants, solvents, acids and bases, and combinations thereof.

23. The method of claim 22 wherein said degrading chemical is a mucolytic agent selected from the class consisting of N-acetyl-L-cysteine, Amboxol, Bromhexine, and combinations thereof.

24. The method of claim 23 wherein said mucolytic agent is a solution of 1% N-acetyl-L-cysteine and 5 percent, by weight of said solution, of NaOH.

25. The method of claim 1 additionally including a step of subjecting said analyte substance to analysis effective to determine at least the presence of said analyte chemical in said analyte substance.

26. The method of claim 25 wherein said analysis is performed by mass or ion mobility spectrometry; electrophoresis; fluorescence, phosphorescence, photoluminescence, infrared, Raman, or surface-enhanced Raman spectroscopy; or gas, liquid or high-performance liquid chromatography.

27. The method of claim 26 wherein said step of subjecting said analyte substance to analysis is effected by surface-enhanced Raman spectroscopy.

28. The method of claim 26 including the additional step of combining said analyte substance with a SERS-active medium that is active for surface-enhanced Raman spectroscopy, said SERS-active medium thereafter being subjected to irradiation, and being used as the source from which surface-enhanced Raman radiation is collected, in performing said surface-enhanced Raman spectroscopy.

29. The method of claim 28 wherein said SERS-active medium contains a SERS-active metal selected from the group consisting of copper, gold, silver, alloys, and mixtures thereof.

30. The method of claim 29 wherein said SERS-active medium is of a form selected from the group consisting of metal colloids in solution, metal colloids deposited on surfaces, metal depositions on surface structures, electrochemically generated metal surfaces, and metal-doped porous materials.

31. The method of claim 30 wherein said SERS-active medium is a metal-doped sol-gel.

32. The method of claim 31 wherein said metal-doped sol-gel is sufficiently porous to permit said analyte substance to be transported therethrough so as to effectively separate said analyte chemical from other components of said analyte substance, with at least a portion of said analyte chemical being retained in said sol-gel in sufficiently intimate proximity to the dopant metal to enable generation, in said irradiation step, of surface-enhanced Raman spectra of said analyte chemical.

33. The method of claim 31 wherein said sol-gel is of a chemical composition effective to extract said analyte chemical from said analyte substance, to thereby improve sensitivity.

34. The method of claim 31 wherein the dopant metal of said sol-gel has an electro-potential that is effective to attract said analyte chemical from said analyte substance, to thereby improve sensitivity.

35. The method of claim 32 wherein the dopant metal of said sol-gel is electropositive silver and is effective to attract a negatively-charged, deprotonated acidic analyte chemical.

36. The method of claim 25 wherein said analysis is also effective to determine the quantity of said analyte chemical in said analyte substance.

37. The method of claim 36 wherein a known amount of said weak acid compound is employed in said step of interacting with said endospores.

38. The method of claim 25 wherein said analysis includes the additional step of passing the said analyte substance though a material that is effective to remove residual spore components and cell debris.

39. The method of claim 38 wherein said material that is effective to remove is selected from the group consisting of filters, membranes, chromatography materials and sol-gels.

40. A method of bacterial contamination analysis, comprising the steps: obtaining a sample comprised of at least one species of bacteria having endospores containing a signature chemical; combining, with at least a component of said sample containing said bacteria, an effective amount of an acidic composition providing, in solution, at least one weak carboxylic acid compound having a dissociation constant of 0.1 to 11, expressed as its pKa value, so as to produce a liquid mixture; allowing said weak carboxylic acid compound to interact with said endospores for a period of time and under conditions sufficient to effect release from said endospores of an analytically detectable form of said signature chemical as an analyte chemical, to thereby produce an analyte substance containing said analyte chemical; and subjecting said analyte substance to analysis effective to determine at least the presence of said analyte chemical in said analyte substance.

41. A method for effecting the release of an analytically detectable form of a signature chemical contained in bacterial endospores, comprising the steps: obtaining a sample comprised of at least one species of bacteria having endospores containing a signature chemical; combining, with at least a component of said sample containing said bacteria, an effective amount of an acidic composition providing, in solution, at least one weak carboxylic acid compound having a dissociation constant of 0.1 to 11, expressed as its pKa value, so as to produce a liquid mixture; and allowing said weak carboxylic acid compound to interact with said endospores for a period of time and under conditions sufficient to effect release from said endospores of an analytically detectable form of said signature chemical as an analyte chemical, to thereby produce an analyte substance containing said analyte chemical, said period of time being from 10 seconds to 5 minutes, and said conditions including ambient temperature and excluding sonication.

* * * * *